United States Patent
Chang

(10) Patent No.: US 11,304,740 B2
(45) Date of Patent: Apr. 19, 2022

(54) MODULAR ORTHOPEDIC CLAMPS

(71) Applicant: Jonathan Chang, South Pasadena, CA (US)

(72) Inventor: Jonathan Chang, South Pasadena, CA (US)

( * ) Notice: Subject to any disclaimer, the term of this patent is extended or adjusted under 35 U.S.C. 154(b) by 147 days.

(21) Appl. No.: 16/918,982

(22) Filed: Jul. 1, 2020

(65) Prior Publication Data

US 2022/0000530 A1 Jan. 6, 2022

(51) Int. Cl.
| | |
|---|---|
| *A61B 17/58* | (2006.01) |
| *A61B 17/60* | (2006.01) |
| *A61F 2/00* | (2006.01) |
| *A61B 17/88* | (2006.01) |
| *A61B 17/28* | (2006.01) |
| *A61B 17/80* | (2006.01) |
| *A61B 17/00* | (2006.01) |

(52) U.S. Cl.
CPC ........ *A61B 17/8866* (2013.01); *A61B 17/282* (2013.01); *A61B 17/2816* (2013.01); *A61B 17/808* (2013.01); *A61B 2017/00473* (2013.01); *A61B 2017/2808* (2013.01); *A61B 2017/2837* (2013.01)

(58) Field of Classification Search
CPC combination set(s) only.
See application file for complete search history.

(56) References Cited

U.S. PATENT DOCUMENTS

| | | | |
|---|---|---|---|
| 5,797,919 A | 8/1998 | Brinson | |
| 5,944,723 A | 8/1999 | Colleran et al. | |
| 6,001,099 A | 12/1999 | Huebner | |
| 6,315,780 B1 | 11/2001 | Lalonde | |
| 8,685,037 B1 | 4/2014 | Jordan | |
| 9,011,507 B2 | 4/2015 | Schelling | |
| 9,339,319 B2 | 5/2016 | Schmuck et al. | |
| 9,532,825 B2 | 1/2017 | Geebelen | |
| 9,550,277 B1 | 1/2017 | Williams et al. | |
| 9,642,641 B2 | 5/2017 | Fernandez Dell'Oca | |
| 9,675,400 B2 | 6/2017 | Katrana et al. | |
| 9,730,741 B2 | 8/2017 | Makhlouf | |
| 9,888,930 B2 | 2/2018 | Hänni et al. | |

(Continued)

FOREIGN PATENT DOCUMENTS

| | | |
|---|---|---|
| CN | 205758659 U | 12/2016 |
| CN | 106388925 | 2/2017 |

(Continued)

OTHER PUBLICATIONS

BD, V. Mueller Catalog, Williams-Style Discectomy Retractors, Jan. 7, 2019, 2 pages, https://catalog1.bd.com/vmueller/williams-style-discectomy-retractors-nl5390-002.html.

(Continued)

*Primary Examiner* — Sameh R Boles
(74) *Attorney, Agent, or Firm* — Maceiko IP

(57) ABSTRACT

An orthopedic clamp to assist in reducing the displacement between bone ends of a fracture, and to position a fixation device, during open fracture reduction surgery is described. The clamp includes a holder to hold the fixation device against the bone. The clamp may also swivel in relation to the holder while the position of the fixation device remains unchanged. The clamp may be modular so that components thereof may be released and/or attached.

15 Claims, 18 Drawing Sheets

(56) References Cited

U.S. PATENT DOCUMENTS

| | | | |
|---|---|---|---|
| 9,999,456 B2 | 6/2018 | Powell et al. | |
| 2012/0271366 A1* | 10/2012 | Katrana | A61B 17/282 606/86 R |
| 2013/0116733 A1 | 5/2013 | Stoll, Jr. | |
| 2013/0345762 A1 | 12/2013 | Dell'Oca et al. | |
| 2015/0313640 A1 | 11/2015 | O'Daly | |
| 2017/0209192 A1 | 7/2017 | Krauss et al. | |
| 2017/0281283 A1 | 10/2017 | Siegler et al. | |
| 2019/0328434 A1 | 10/2019 | Slocum et al. | |

FOREIGN PATENT DOCUMENTS

| | | |
|---|---|---|
| CN | 206836918 U | 1/2018 |
| CN | 108078610 | 5/2018 |
| CN | 207492791 | 6/2018 |
| KR | 10-1681177 | 11/2016 |
| RU | 185903 | 12/2018 |

OTHER PUBLICATIONS

Bradshaw International, Deluxe Tongs, Jan. 7, 2019, 10 pages, https://www.amazon.com/bradshaw-international-25871-Deluxe-Tngs/dp.

Innomed, Inc., Foot & Ankle Instruments, Innomed Small Bone Instruments-Foot & Ankle-Bone Clamps, 2019, 18 pages.

\* cited by examiner

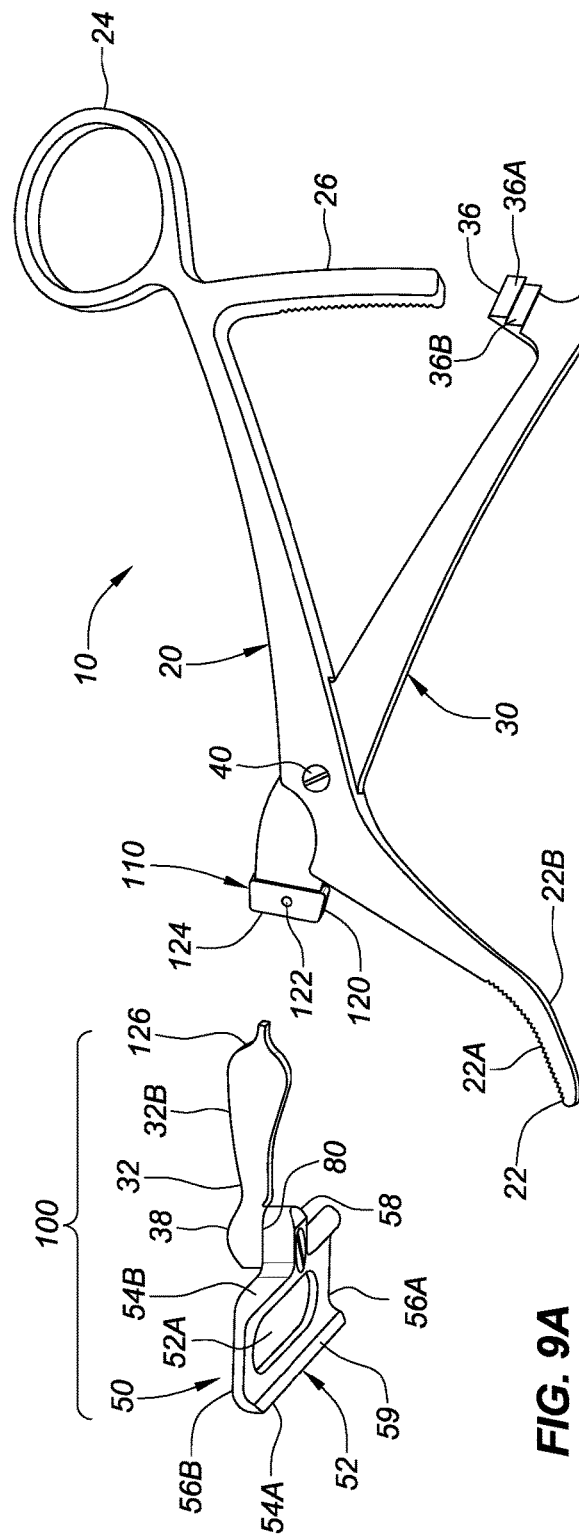
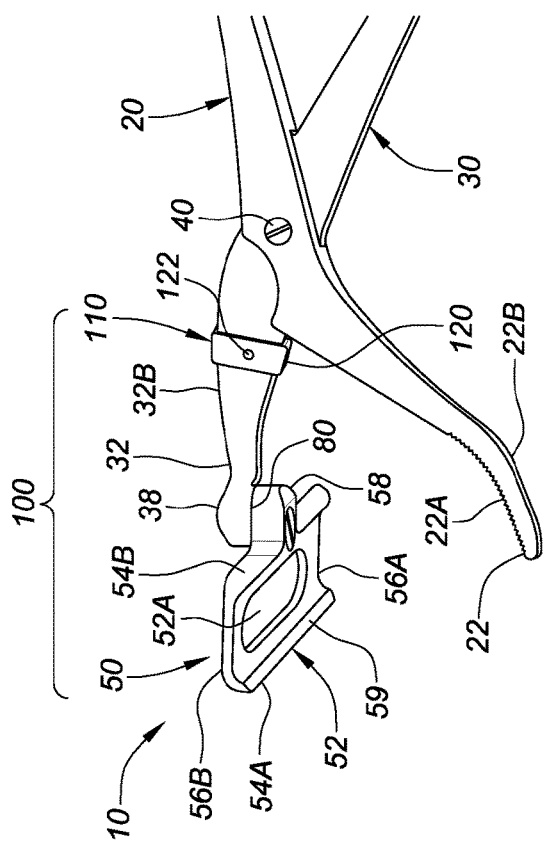
FIG. 9A
FIG. 9B

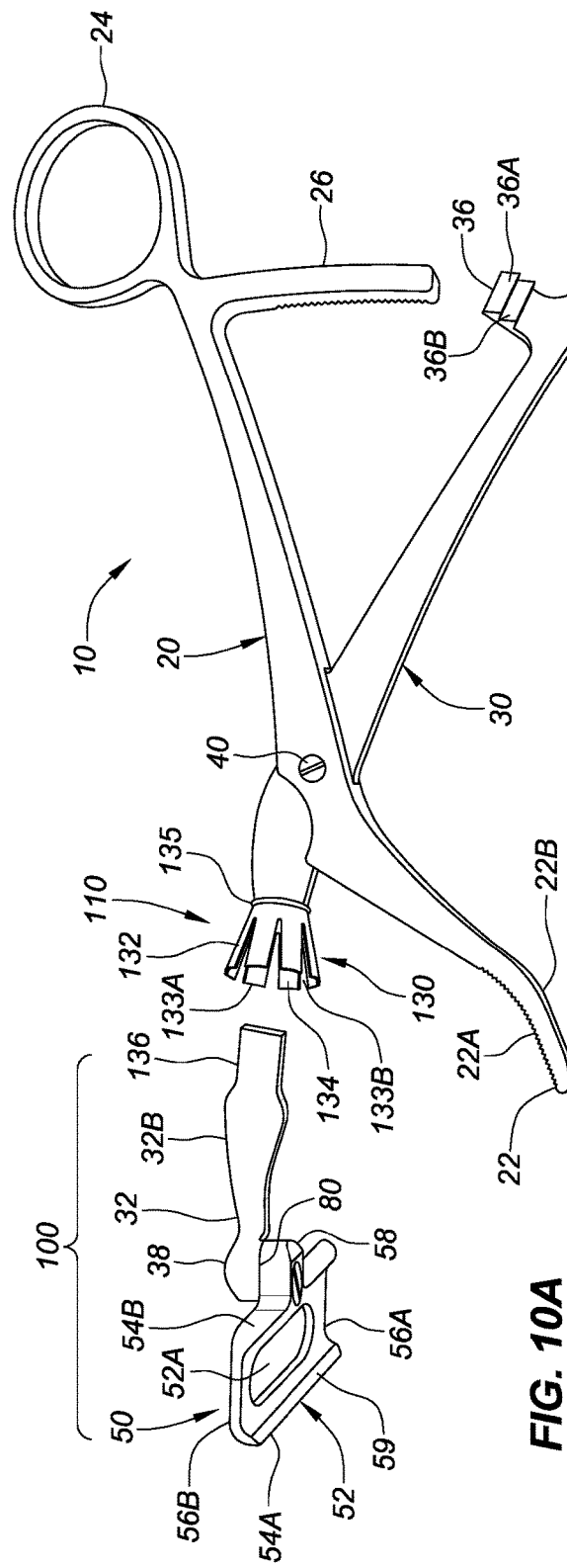
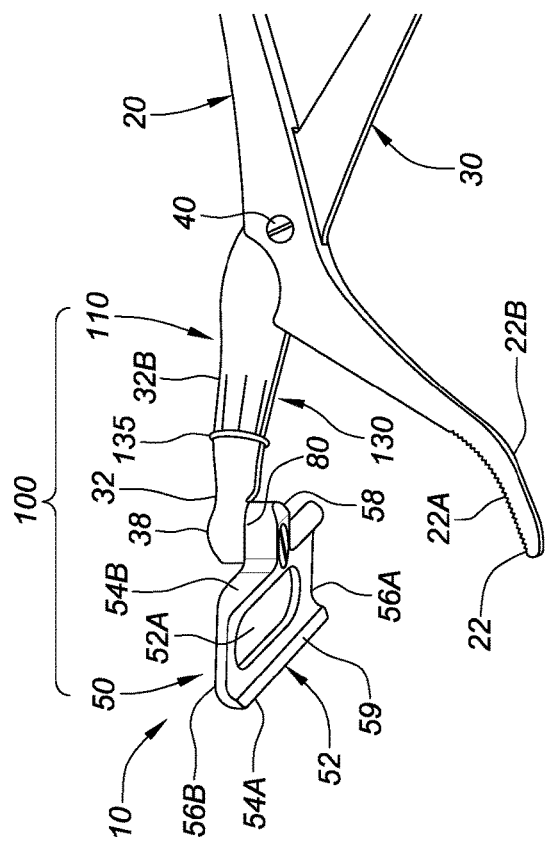
FIG. 10A
FIG. 10B

MODULAR ORTHOPEDIC CLAMPS

CROSS-REFERENCE TO APPLICATIONS INCORPORATED BY REFERENCE

The contents of U.S. application Ser. No. 16/351,417 and International Application No. PCT/US2020/022481 are incorporated herein by reference as if fully set forth herein.

FIELD OF THE INVENTION

The current invention generally relates to devices and techniques to facilitate orthopedic surgeries, including clamps and devices for use in open fracture reduction surgery to maintain a reduction, provide alignment and/or to position an internal fixation device during surgery. The current invention also relates to modular clamps and devices that include releasable components that may be detached and attached to the clamp or device, where such releasable components may be disposable or reusable.

BACKGROUND OF THE INVENTION

When a bone is fractured, the broken bone ends and/or or other parts of the bone may become displaced. When the displacement is significant, surgery is often necessary to directly access the broken bone ends and/or other bone pieces, so that the fracture may be reduced, and so that an internal fixation device, such as a plate, may be attached to broken bone ends and/or other bone pieces to hold them in place while the bone heals.

In open reduction surgery, various clamps and other devices have been used to reduce the fracture and align the broken bone ends and/or other bone pieces so that they are in proper position prior to attaching the internal fixation device. However, while existing clamps may be effective in reducing the fracture, they do not aid in attaching the plate or other internal fixation device. Furthermore, existing clamps must typically be removed when the internal fixation device is installed, because otherwise the clamp would be in the way of where the internal fixation device would be installed, or would otherwise interfere with installation.

As a result, a surgeon must remove the reduction clamps so that the internal fixation device may be installed. This often requires the surgeon to maintain the reduction by hand. For example, the surgeon holds the broken bone ends together by hand while a plate is attached to the broken bone ends with screws.

This generally results in a suboptimal process because the reduction may not be fully maintained by the surgeon and/or the alignment of the broken bone ends may not be maintained in an optimal position. This process may also lengthen the duration of the surgery which is also suboptimal because it is preferred to reduce the time that a patient is under anesthesia.

Certain existing clamps have attempted to hold a plate in place. However, such clamps had fixed angles and/or had a small footprint such that they would rarely accommodate or fit a plate; and even if they did, they would not securely hold the plate but would instead allow it to rotate or otherwise move from its desired position. Furthermore, such clamps have typically not been intended for fracture reduction. Other existing clamps that have attempted to hold a plate in place have also involved additional components, such as temporary fixing plates, that may tend to make the overall open fracture reduction surgery more complicated and/or longer.

Some of these other existing clamps are very invasive and would require excessive dissection of the tissue surrounding the fracture. Other existing clamps would simply be too large or cumbersome to use for open fracture reduction surgery.

Accordingly, there is a need for a surgical device that facilitates open fracture reduction surgery by assisting in the reduction of fractures and the placement and installation of internal fixation devices. There is also a need for a more efficient process of performing open fracture reduction surgery.

Existing clamps typically comprise an assembly in which all components of the clamp are integrally attached to each other. As such, none of the components are modular or readily detachable, if detachable at all, from the rest of the clamp. This lack of modularity may create issues regarding the duration and efficiency of the open fracture reduction surgery, and patient recovery time, as well as the cost of the open fracture reduction surgery.

For example, an x-ray may reveal a fracture before surgery. However, the x-ray may not fully inform the surgeon of all the circumstances inside the patient that will dictate how the forthcoming surgery will actually be performed; e.g., circumstances that may only be known after incisions are made in the patient and the fracture site opened and revealed. To this end, an x-ray may not fully apprise the surgeon of the type and/or size of the plate or other fixation device, which should be used to reduce and secure the fracture before incisions are made in the patient and the fracture site is revealed.

Before surgery, a surgeon may rely on an x-ray to ready a certain type and/or size of plate and instrument to position that plate. But after incisions are made and the fracture site is opened, the surgeon may see that another type and/or size of plate and instrument is necessary. In this situation, valuable time may be lost readying another plate and instrument. This may lengthen the time of the surgery, and thus lengthen the time the patient is under general anesthesia, which is generally disfavored. Furthermore, it is common to apply a tourniquet in many orthopedic limb surgeries. And given that the inflation pressures, duration and release guidelines for the use of tourniquets are not entirely established, lengthening the time that a tourniquet is applied is also disfavored. Beyond the foregoing, increasing the surgery time also increases costs.

Accordingly, there is a need for a modular orthopedic clamp that would allow a surgeon to easily change components of the clamp to address the actual requirements of the open fracture surgery to be performed. This may occur, for example, when the actual requirements of the surgery differ from what the surgeon assumed or expected before opening up the patient, based on an x-ray.

The lack of modularity of existing devices may also increase cost of the instruments needed for surgery, as well as the overall cost of medical care. For example, the tongs of an orthopedic clamp may generally be reusable or may be used for different types of surgeries. On the other hand, however, the component of the clamp which may hold the implant or fixation device in place for attachment to the bone ends of a fracture may be suitable only for a single use or for a specific type of surgery.

For example, the size and configuration of a plate used for ankle surgery may differ from those of the plate used for surgery involving larger bones. Furthermore, upon opening the patient to review the fracture site, the surgeon may see that a different sized or configured plate may be necessary. Still further, the plate-positioning portion of the clamp may wear out when used for multiple surgeries, while the tong portion may generally not wear out.

Because existing clamps generally comprise components that are attached together and are not intended to be disassembled, a surgeon or medical facility needs to have a number of clamps available to accommodate differently sized or configured plates for different types of surgeries, even though the tong portion of the device could be used with different plates. Also, where the plate-positioning portion of the clamp wears out due to repeated use, but the tong does not wear out, complete clamp assemblies would still need to be maintained by the surgeon or medical facility.

Accordingly, there is also a need for a surgical device or clamp that comprises modular components that may be detached from each other, where certain components may be disposable and others may be reusable or suitable for different types of surgeries.

There is also a need for an orthopedic clamp comprising desirable materials, such as radiolucent materials, that would not interfere with an x-ray taken, for example, during surgery to determine whether the plate has been properly positioned over the fracture site.

SUMMARY OF THE INVENTION

An aspect of the invention is that the surgical clamp may be used to reduce a fracture, and to maintain the reduction, while also including a plate holder, or frame, to hold the plate or other internal fixation device in place for installation. This is a significant advance because with the clamp of the current invention, a reduction may be more easily and accurately maintained, and the reduction need not rely on the surgeon maintaining the reduction by hand. This is also a significant advance because reduction clamps, unlike those currently existing, need not be removed.

Another aspect of the invention is that different sizes and shapes of plates and other internal fixation devices may be held in place by the clamp. To accommodate different shapes and sizes, the frame of the plate holder may comprise rectangles and other shapes of different sizes. The frame may also be curved to accommodate holding a curved plate in place. It is preferred that the frame be sized so as to securely hold the plate or other internal fixation device, e.g., to avoid wiggle room or rotation of the plate relative to the frame.

Another aspect of the invention involves the frame having a window or cutout that provides access to the bone where the screws or other attachment means will be installed. As such, the clamp of the current invention allows the installation of screws while holding the internal fixation device in place, and also while maintaining the reduction. In an alternative embodiment, the window or cutout may be solid material with holes cutout to correspond to where the screws or other attachment means will be installed to secure the plate to the bone.

Another aspect of the invention involves the tool having a swivel between the plate holder and the rest of the tool. This allows the surgeon to swivel the frame of the plate holder to the desired orientation along the bone, while holding the tongs of the tool in the same place, thereby allowing the surgeon to better maintain the reduction. In an alternative embodiment, the plate holder may be fixedly attached to the tool. While the adjustability of a swivel does not exist in this embodiment, the fixed configuration may be suitable for surgery where the tool is generally held at a certain angle.

Other aspects of the invention render the device easier to use during surgery. For example, the tool of the current invention preferably includes a ratchet mechanism to lock or otherwise hold the tongs in the desired position. In this manner, pressure may be exerted on opposite or different directions on the bone(s) thereby maintaining the reduction and freeing up the surgeon to perform other tasks in the surgery.

Another aspect of the invention involves making an open reduction surgery more efficient. For example, reduction clamps need not be removed so that the internal fixation device may be installed. And time is not spent ensuring that the reduction is properly maintained by the surgeon's hand before and during installation of the internal fixation device. Time is also not spent manipulating additional components, such as temporary plates. As such, the duration of the surgery, and the amount of time that the patient is under anesthesia, may be reduced. The surgery may also be rendered less complicated thereby making the surgery more of an optimal situation.

The current invention may also make the surgery more efficient by aiding in the retraction of the skin to provide access to the fracture. That is, the clamp of the current invention allows for an upright placement on the fractured bone that may help retract the skin, which in turn, may avoid the need for a separate skin retractor during surgery. As such, the surgeon may perform the surgery while having to position and/or manipulate fewer surgical tools, which may decrease the time of surgery. Furthermore, a person who would otherwise be required to assist in the surgery by manipulating the skin retractor may be unnecessary.

Another aspect of the invention involves the modularity of components comprising or included in the orthopedic clamp. To this end, the frame or component that holds the implant or other fixation device against the fractured bone ends may be releasable or separable from the tongs or the rest of the clamp or surgical instrument. The component or components that may be released from the rest of the clamp may vary. For example, the frame and swivel may form a releasable portion that is releasable from a tong. As another example, the frame or plate holder may form a releasable portion that is releasable from the tong; or releasable from the swivel or from a pin which is attached to, or forms part of, the tong. As another example, the frame and swivel as well as a length of tong may form a releasable portion that is releasable from the remaining length of the tong.

The releasable portion may be attached and detached from one of the tongs, or from the swivel, by different types of release mechanisms. The release mechanism may provide the release function by mechanical, magnetic or other means, or a combination thereof. In general, it is preferred that the release mechanism be relatively compact so that it does not interfere with the use of the clamp. It is also preferred that the release mechanism may withstand forces imparted by a surgeon when squeezing the clamp during surgery.

For example, the releasable portion of the clamp may include a pin that engages a bored hole at the end of one of the tongs. The pin may include a ball or bearing that engages a groove formed in the wall of the hole. In another embodiment, the release mechanism may include a magnetic lock with a button that, when pushed, serves to release the releasable portion of the clamp. In another embodiment, the release mechanism may include a sleeve with a hole that receives a pin of the releasable portion, wherein the sleeve may include slots that allow the hole diameter to expand or contract. In this embodiment, the release mechanism may also include a ring or collar that slides along the sleeve and that serves to contract the hole diameter to tighten the sleeve and hold the releasable portion.

In another embodiment, the release mechanism may comprise a chuck that receives the releasable portion, and a key that serves to tighten the chuck around the releasable portion. In other embodiments, the release mechanism may comprise a keyless chuck, keyless chuck with a secondary lock mechanism, wire collet, Jacobs chuck, Trinkle chuck or any other suitable release mechanism.

In another embodiment, the release mechanism may include a flip switch or quick connect mechanism. In this embodiment, the release mechanism may be attached to, or form part of, a tong. The release mechanism may include a retractable pin having different diameters to engage a slot and a hole in the frame. In an extended position, a smaller pin diameter may engage the slot in the frame. A lever may be used to retract (and extend) the pin. When retracted, a larger pin diameter may engage the hole, and this larger diameter may be larger than the slot width, thereby preventing the frame from disengaging the pin. The pin may also support the frame's bottom. The frame may swivel as the bore rotates about the pin, or the frame may rotate along with the pin. As an alternative, the flip switch mechanism need not provide a swiveling function of the frame relative to the clamp.

It is preferred that the release mechanism allows a surgeon to quickly and efficiently attach the desired plate or plate assembly to the clamp, and if necessary, to release the plate or plate assembly. The plate or plate assembly may be color coded to help the surgeon quickly identify the desired plate or plate assembly. It is also preferred that the release mechanism be relatively compact so that it does not impede the other functions of the clamp described herein.

Another aspect of the invention involves the materials comprising the clamp. For example, the frame that holds the plate or other fixation device to the fractured bone ends may comprise carbon fiber or some other radiolucent material, so that the bones under the clamp may be visible on an x-ray. The tong portion of the clamp may also comprise a radiolucent material. It is preferred that the materials comprising the frame are sufficiently rigid and durable to withstand the squeezing forces exerted on the clamp by the surgeon during surgery. It is also preferred that the materials are not overly brittle.

In another aspect of the invention, the components of the clamp assembly and/or plate or other fixation device may be colored differently. For example, a certain sized plate may be configured to work with a certain clamp/plate. Where they are both the same color, and other clamp/plate combinations are other colors, the color difference allows the surgeon to more quickly identify the surgical instrument and implant to use. In another aspect of the invention, the releasable portion of the clamp may be disposable.

Other aspects of the invention are discussed herein.

BRIEF DESCRIPTION OF THE DRAWINGS

FIG. 9A shows an exploded view of a release mechanism involving a magnetic lock and release button. FIG. 9B shows the release mechanism of FIG. 10A engaging the releasable portion.

FIG. 10A is an exploded view of a release mechanism involving an expandable sleeve and sliding ring. FIG. 10B shows the release mechanism of FIG. 10A engaging the releasable portion.

DETAILED DESCRIPTION OF THE PREFERRED EMBODIMENTS

Figure 1:
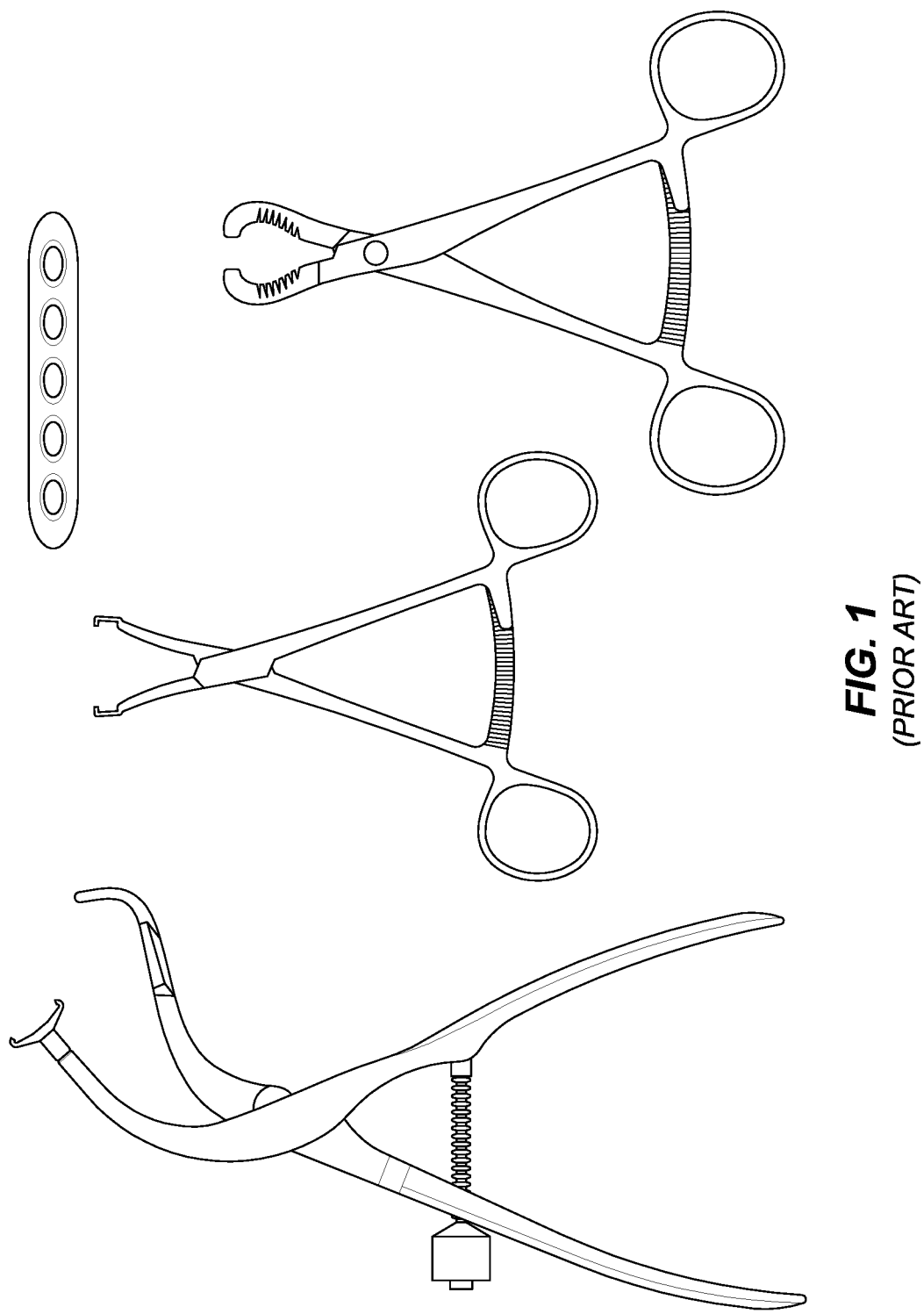
FIG. 1 is a picture showing existing fracture reduction clamps and an internal fixation device comprising a plate.

The current invention is now described with reference to the figures. FIG. 1 shows several existing types of clamps, as well as an existing internal fixation plate. Generally, the existing clamps may be used to reduce the fracture, and maintain the reduction, but at least one of the tongs will be in the way of installing the plate. Accordingly, these existing clamps must typically be removed in order to install the plate.

As noted above, this requires the surgeon to maintain the reduction by hand while also positioning the plate and holding the plate in place while installing the screws or other attachment means used to fix the plate before the patient is closed. This is a suboptimal process because the integrity of the reduction or the alignment of the broken bone ends or other bone pieces may be lost or reduced. This is also a suboptimal process because it is inefficient and may increase surgery time and the time that the patient is under anesthesia.

Referring to FIGS. 2-5, the current invention is now described in more detail. Orthopedic clamp or device or tool 10 may include first or lower tong 20 and second or upper tong 30 that may be moveably coupled to each other. First or lower tong may include distal or tong end 22 which, when tool 10 is used, may engage the bone being reduced and may serve to press from a first direction, e.g., the underneath or the bottom of a reduction, or the distal side of the reduction located away from the surgeon. Tong end 22 may include serrated section 22A to help it securely engage the bone to be reduced.

Distal or tong end 22 may comprise a curved and/or tapered end, which allows it to be placed on the distal, opposite or other side of the bone to be reduced and plated without needing to dissect more soft tissue around or from that side of the bone. This may generally improve the healing potential of the fracture.

In an alternative embodiment, distal or tong end 22 may be configured to include a rectangular or curved piece that may support more of a length of the distal, underside or other side of the bone(s). Lower tong 20 may also include a handle having a finger hole 24 and positioning or locking stem 26. Stem 26 may include a series of ridges, peaks/valleys or teeth 26A, 26B, etc.

Second or upper tong 30 may include distal or tong end 32, and a handle having finger hole 34 and positioning or locking tab 36. Tab 36 may include one or more ridges or high points 36A, 36B, etc. that may engage with the teeth 26A, 26B, etc. of stem 26 to lock the tool 10 in a desired configuration. Tongs 20, 30 may be moveably coupled to each other or joined by a threaded screw arrangement or other form of attachment 40 that preferably allows tongs 20, 30 to move or rotate relative to each other about attachment 40. In a preferred embodiment, stem 26 and tab 36 comprise a ratchet to lock or hold tongs 20, 30 in the desired position once determined by the surgeon.

The distal end 32 of upper tong 30 may interface with holder, insert or cutout assembly 50 that may be configured to hold or position a plate or other fixation device in the location at which it will be attached to the fractured bone(s).

Figure 6:
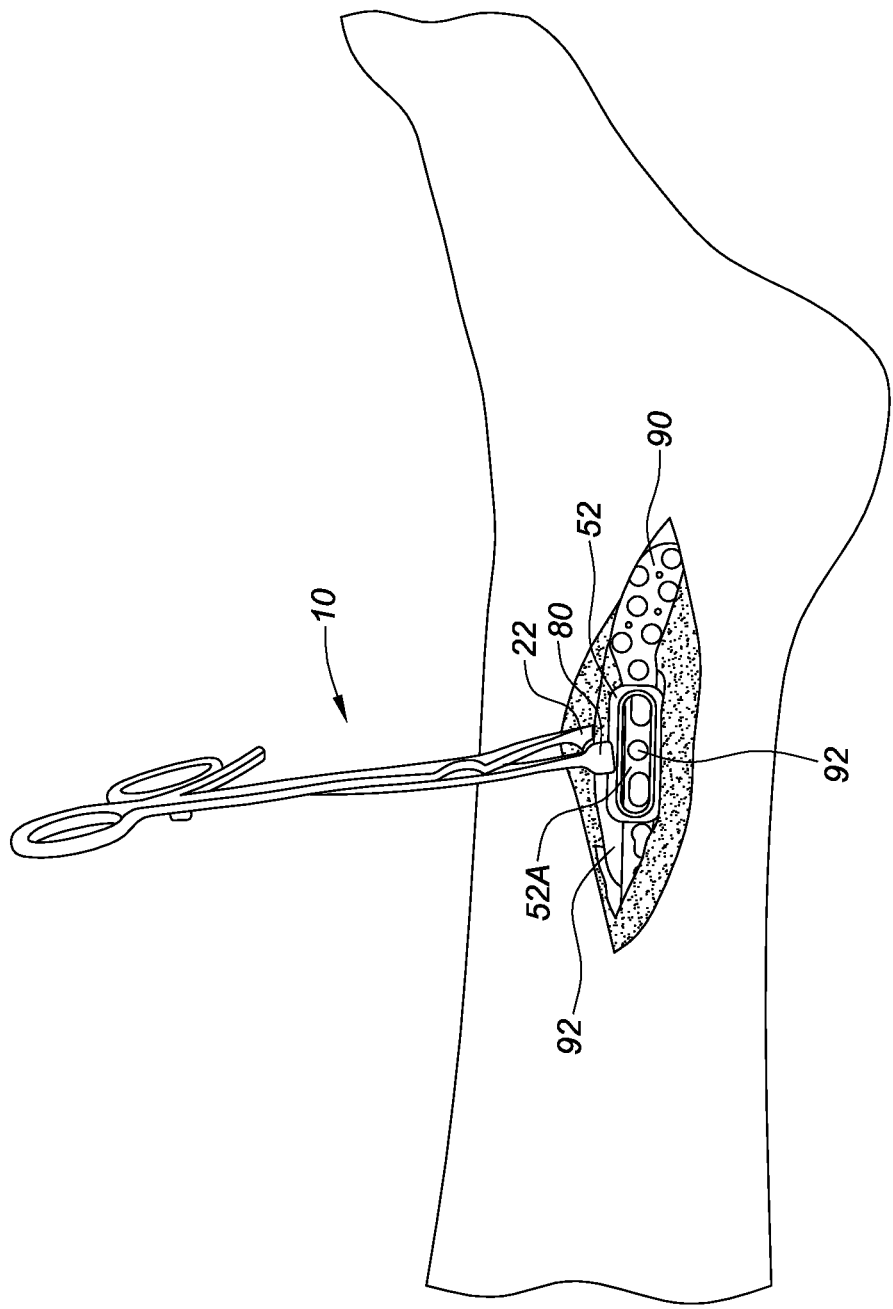
FIG. 6 shows a clamp and fixation device holder during surgery.

Holder 50 may include frame or cutout 52 that may be attached to tong end 32 via swivel 80. Frame 52 may generally serve to position the plate 90 (as shown in FIG. 6) or other internal fixation device, as well as to hold plate 90 in place on bone 92 while screws or other attachment means are installed. That is, plate 90 may be held between frame 52 and the bone 92 so that tool 10 presses plate 90 towards the bone 92 in the desired location so as to securely hold it in place. In this manner, when the surgeon squeezes tong handles 24, 34 together, frame 50 and distal end 22 exert forces in opposite or other directions towards each other which serves to maintain the reduction and hold plate 90 in place for installation.

In this manner, the current invention represents an advance over certain existing tools that may provide a socket in which to position the plate, e.g., the device shown at the link below:

http://www.innomed.net/smallbone_footankle_clamps.htm#DuncanClampFt

However, in those existing tools, the plate merely rests on top of the tool and is not clamped between the tool and the bone. As such, the plate is not securely held in place with respect to the bone. Furthermore, in these existing tools, the plate may rotate or wiggle relative to the tool which further adds to issues because the plate is not securely held in place.

Figure 2:
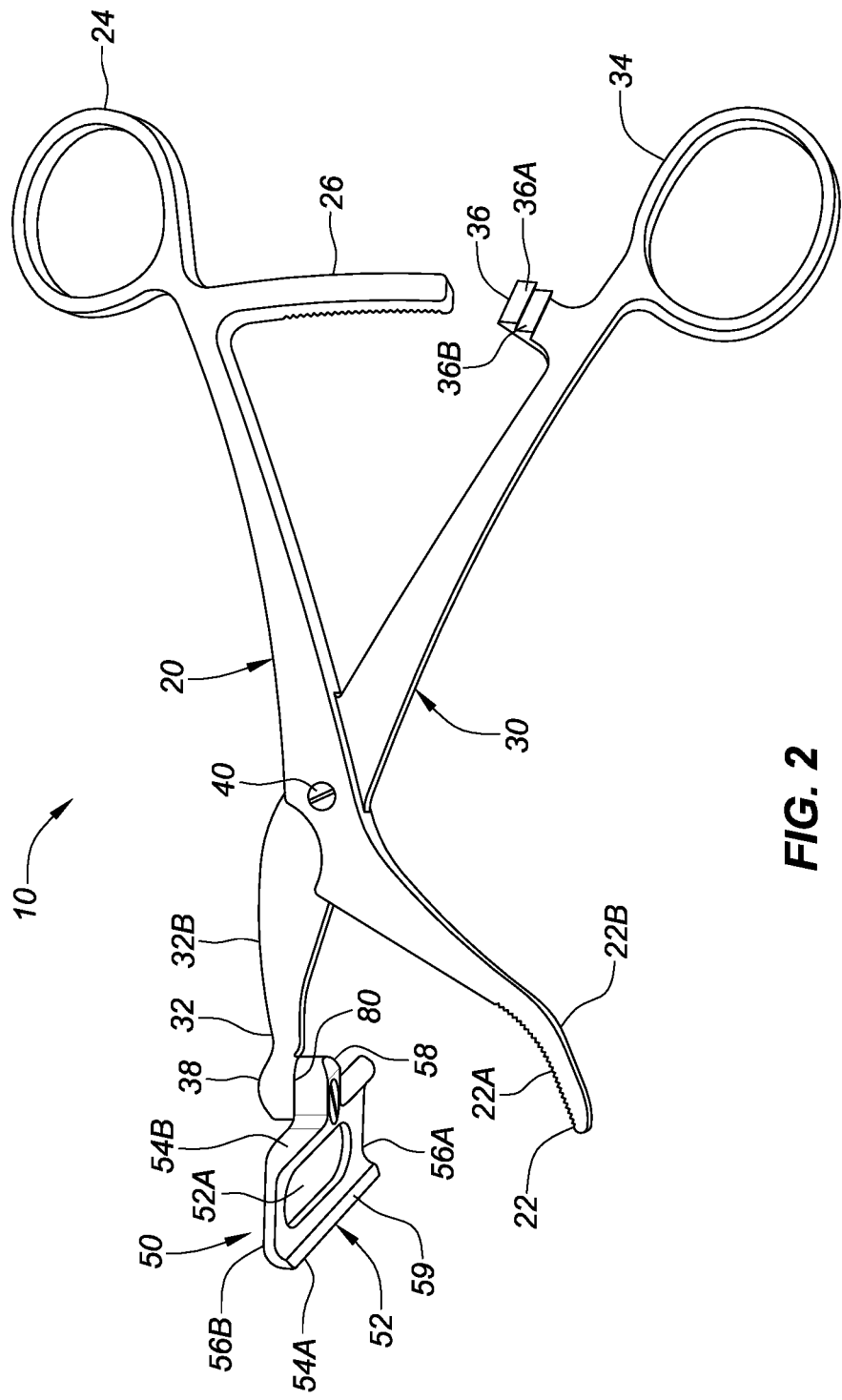
FIG. 2 is a side perspective view of a clamp and fixation device holder.
Figure 4:
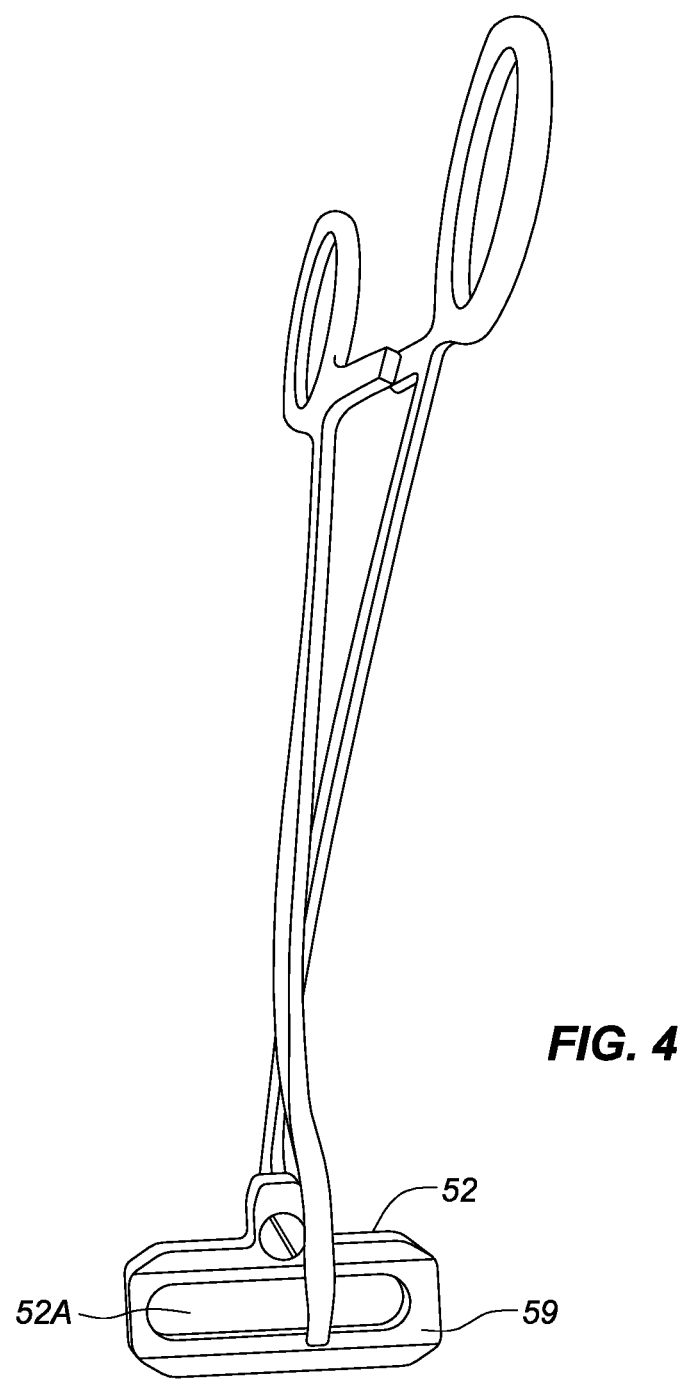
FIG. 4 is a rear perspective view of a clamp and fixation device holder.
Figure 5:
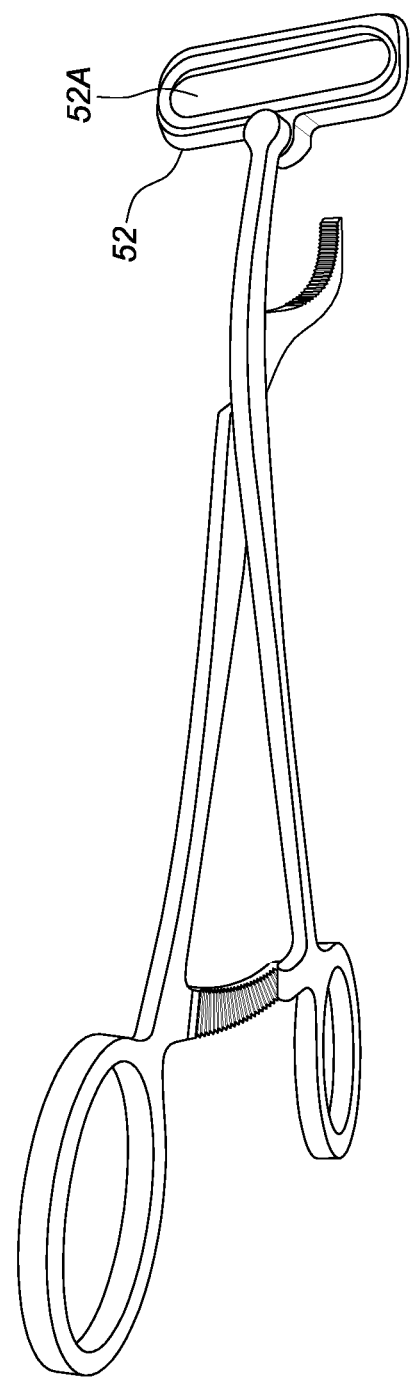
FIG. 5 is a front perspective view of a clamp and fixation device holder.

To facilitate the swiveling of frame 52 relative to upper tong 30, tong end 32 may include threaded hole 38 and plate holder assembly 50 may include tab 58. The swivel 80 attachment between tab 58 and hole 38 may comprise a bolt or screw (as shown in FIGS. 2 and 4), bearing, bushing or other attachment mechanism that allows frame 52 to swivel relative to upper tong 30. It is preferred that the attachment mechanism allows the smooth swiveling of frame 52 relative to tong 30 so that tool 10 may be swiveled without disrupting the position of plate 90. As discussed in more detail later, the swiveling capability allows clamp 10 to maintain the reduction while allowing the surgeon a degree of freedom in placing the plate or other internal fixation device, and to perform other tasks such as installing the screw to attach the plate to the bone(s).

Frame 52 may be configured to accommodate various shapes and sizes of plates or other internal fixation devices. It is preferred that frame 52 engage at least some of the edges of the plate while providing access to the upper surface of the plate, i.e., it is preferred that frame 52 surround a "window" or opening 52A that allows access to the part of the plate within the perimeter of frame 52 as it engages the reduced bone ends. This allows the surgeon to install screws or other attachment means within window 52A and through the plate and into the bone. Additionally, frame 52 securing plate 90 to the bone(s) also allows the surgeon to install screws outside the perimeter of frame 52.

In the embodiment of tool 10 shown in FIGS. 2-5, frame 52 may be shaped as a rectangle comprising sides 54A, 54B and ends 56A, 56B. This configuration may be preferred for a fibular fracture reduction. The lengths of sides 54A, 54B and/or the ends 56A, 56B may be varied to accommodate different sized rectangular plates. However, frame 52 may comprise other shapes and sizes. Furthermore, frame 52 may be curved in both the longitudinal and/or transverse dimension(s) to accommodate curved plates or other internal fixation devices. Accordingly, tool 10 of the current invention is not limited for use with fibular fractures. Indeed, clamp 10 of the current invention may be used for open reduction surgeries on a number of other bones with their own particular shapes, sizes and/or configurations.

Figure 3:
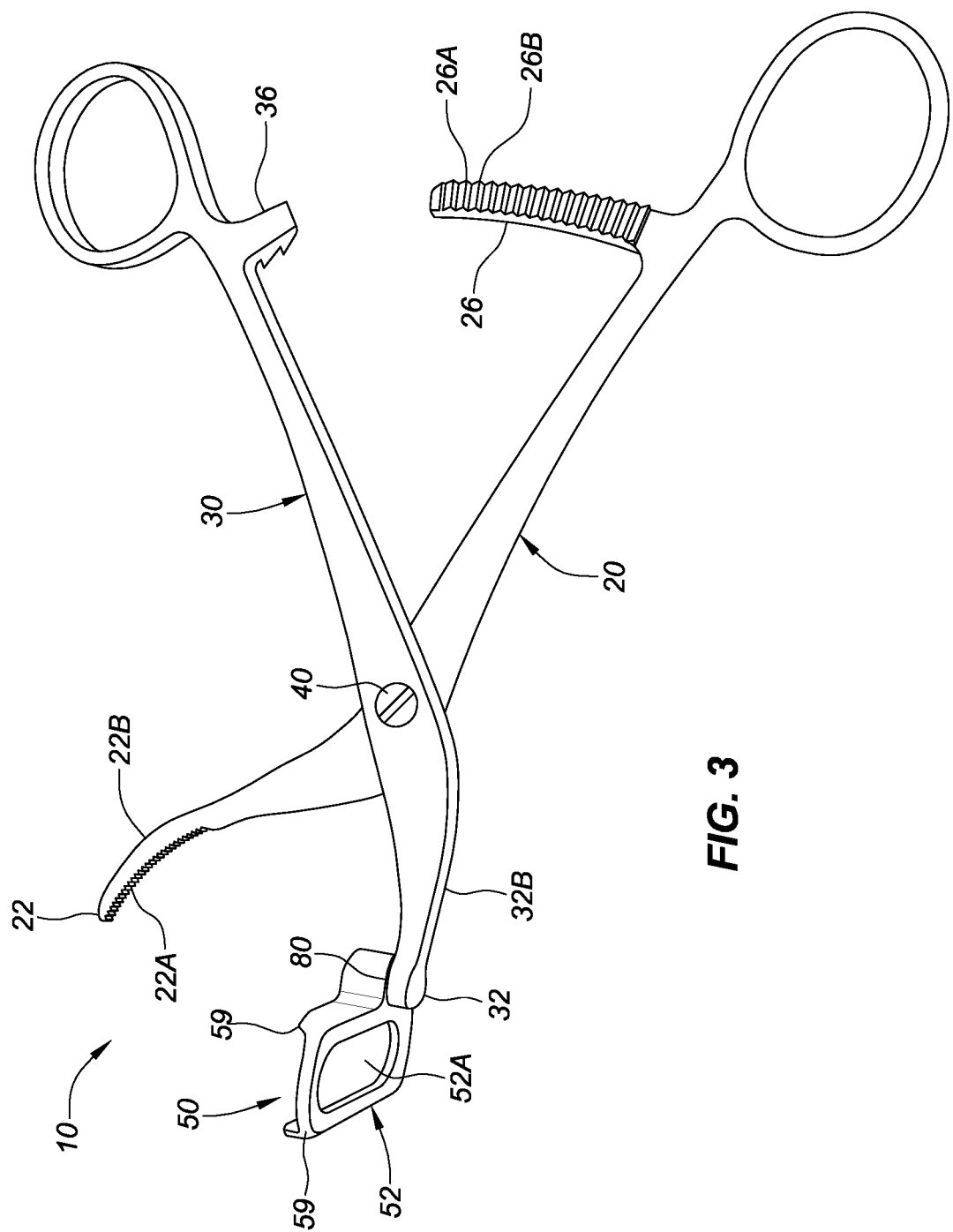
FIG. 3 is a side perspective view of a clamp and fixation device holder.

As best shown in FIGS. 2-4, frame sides 54A, 54B may extend downward to form lip 59 that may help contain and position the plate to be installed. This is in addition to the fact that tool 10 pushes the plate towards the bone(s). As such, tool 10 provides a secure placement and positioning of the plate unlike prior devices.

In the embodiment shown in FIGS. 2-5, frame ends 56A, 56B do not have lip 59, and the plate to be installed may extend beyond frame 52. However, in other embodiments, lip 59 may extend around the periphery of frame 52 thereby providing a "socket" type holder for the plate being installed.

Beyond the unique and innovative characteristics of tool or clamp 10 described above, the current invention also provides for a safer, more accurate and more efficient way to conduct an open fracture reduction surgery. To this end, the current invention fills an unmet need for a device that may reduce the fracture, and then better maintain the fracture reduction while also holding the repair plate or other fixation device in its proper position at the same time without having to remove the reduction clamps. As noted above, this may generally eliminate the human aspect of maintaining the reduction by hand, which may lead to misalignment and also prolong the length of the surgery and the time the patient is under anesthesia.

Furthermore, the swiveling 80 of holder or frame 52 with respect to tong 30 preferably holds the plate against the bone while the angled opposite tip 22 allows for positive tightening without the need for any further soft tissue dissection. By holding onto the plate itself, the reduction will not be lost while positioning the properly sized plate on the reduced fracture, and window 52A also allows for drilling of multiple holes in the plate under frame 52 without moving clamp 10. This improves upon current available equipment that does not allow any of these maneuvers to occur.

FIG. 6 shows tool 10 in use during an open fracture reduction surgery of a fractured fibula 92. As shown, tool 10 is positioned in the desired location to both reduce the fracture and locate the plate or other fixation device for installation. Once tool 10 is thus positioned, the ratchet mechanism 26, 36 holds tongs 20, 30 in a fixed position relative to each other.

As also shown in FIG. 6, distal or tong end 22 helps maintain reduction of the fracture by pressing it towards the surgeon from the other side of the bone. Because distal or tong end 22 may be configured as a tapered and pointed end, it can be seen how further dissection of the tissue around the fibula need not be further dissected, which would be the case if tong end 22 were configured with a transverse piece (that would be axially aligned with the fibula).

The current invention may also make the surgery more efficient by aiding in the retraction of the skin to provide access to the fracture. That is, the clamp 10 of the current invention allows for an upright placement on the fractured bone 92 that may help retract the skin, which in turn, may avoid the need for a separate skin retractor during surgery. To this end, the section or strut 22 of tong 20 that may be positioned on the distal side of the reduced fracture may be in contact with, and help retract, the skin on that side of the incision that may help avoid the need for a separate skin retractor. Similarly, the section or strut 32 of tong 30 may also help retract the skin when it is in contact with the skin.

As such, the surgeon may perform the surgery while having to position and/or manipulate fewer surgical tools, thereby decreasing the time of the surgery. Furthermore, an assistant who would otherwise be required to manipulate the skin retractor may be unnecessary.

Frame 52 preferably secures plate 90 against the fibula 92. As shown, window or cutout 52A provides ready access to plate 90 and plate holes 92 through which screws or other attachment means may be installed. In addition, frame 52 holds plate 90 in place while plate holes 92 outside of frame 52 are also accessible.

The unique benefit of swivel 80 is also shown in FIG. 6. That is, once frame 52 and plate 90 are located in the desired position, swivel 80 allows tool 10 to be rotated relative to frame 52 without moving plate 90. To this end, it is preferred that the swivel connection 80 allows the smooth and/or unhindered rotation of tool 10 relative to frame 52 and plate 90 so that plate 90 may remain in the desired located while tool 10 is swiveled. The smooth swiveling operation may be provided by a bearing, bushing, nut/bolt or other suitable mechanisms. Maintaining the position of plate 90 while swiveling tool 10 may be desired especially where screw holes may have been drilled into the bone to be plated, and it is optimal for plate 90 to remain in the position so that the screw holes in plate 90 match up with screw holes drilled into the bone.

The swiveling capability of tool 10 may also be facilitated by distal or tong end 22 being tapered or pointed, because the tip of distal end 22 may contact the bone and still rotate relative thereto without cutting into any surrounding tissue and/or requiring any further dissection. The swiveling capability of tool 10 is beneficial, for example, to provide more space for the surgeon to install the screw and to manipulate the tools necessary to do so.

The frame 52 and its lip 59 are preferably configured in a curved fashion, i.e., curved along its ends 56A, 56B to correspond to and better hold a curved plate 90 that is, in turn, configured to generally correspond to the curvature of the fibula or other bone to be plated. Furthermore, the foregoing may all occur while tool 10 maintains the fracture reduction and does not require removal of reduction clamps and/or require the surgeon to maintain the reduction by hand while installing the plate 90. To this end, the locking ratchet connection 26, 36 may keep tongs 20, 30 in the desired locked position so as to maintain pressure from opposite or different directions against the bone(s). In this manner, the reduction is maintained while the surgeon is free to concentrate on the tasks associated with fixing plate 90 to the bone(s).

Embodiments of the current invention where clamp 10 is modular where certain components are releasable from the rest of clamp 10 are now described with reference to FIGS. 7-10. Generally, it is preferred that plate holder assembly 50 may be releasable from the rest of clamp 10. However, other or additional components or parts of clamp 10 may also be releasable. Regardless of what components comprise the releasable portion, it is preferred that the releasable portion may be readily attached or detached from clamp 10. This way, when the desired plate 90 has been chosen, the appropriate plate holder assembly 50 that corresponds to that plate 90, may be readily installed on clamp 10. This preferably reduces the time of surgery and time that the patient is under anesthesia. The efficient installation of the releasable portion may be especially beneficial when opening up the fracture site reveals that the plate 90 and plate holder assembly 50 that should be used is different than what might have been expected based on the pre-surgery x-ray.

Figure 7:
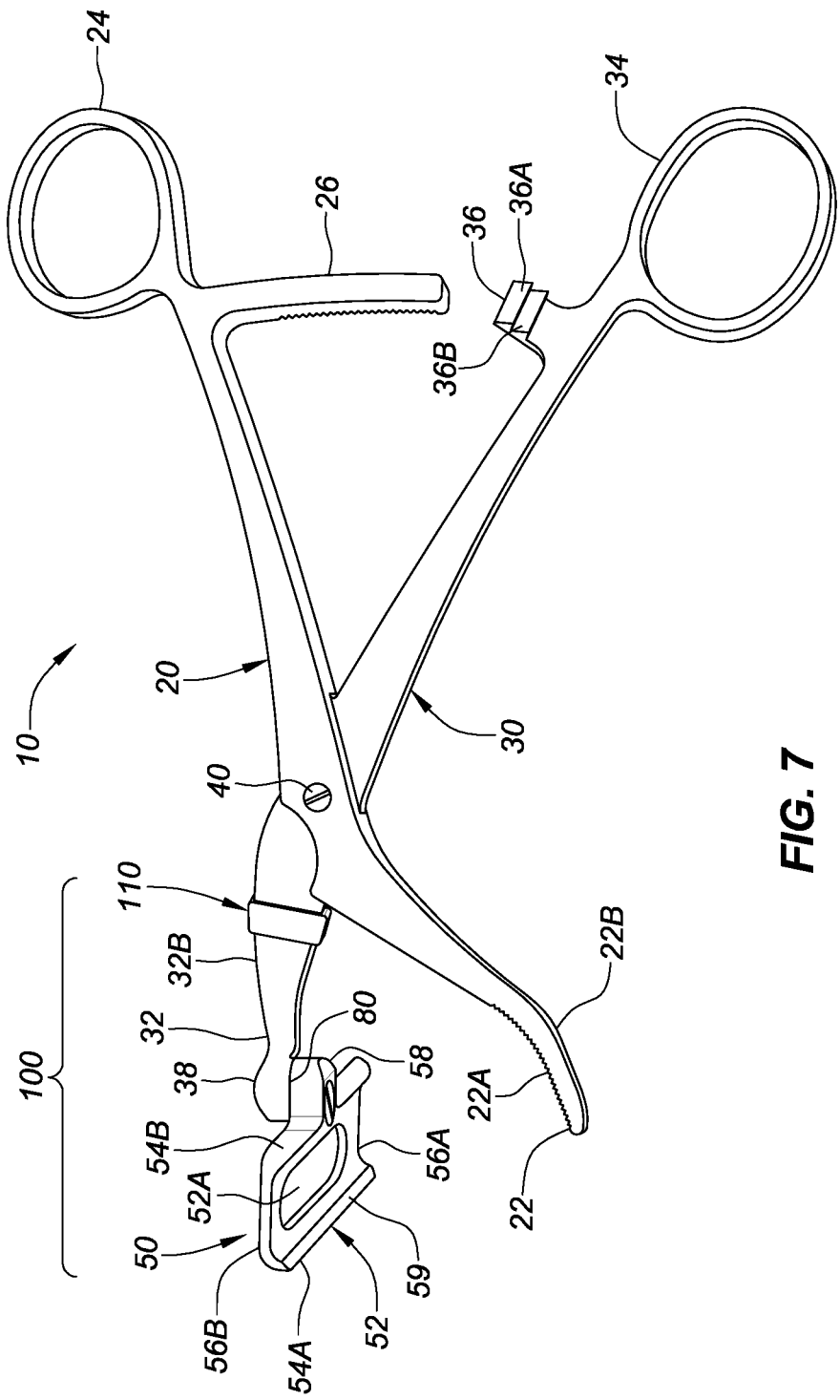
FIG. 7 shows an orthopedic clamp with a releasable portion including a plate holder assembly and part of a tong, and a release mechanism.

As noted above, the components which may comprise the releasable portion may vary. FIG. 7 shows the releasable portion 100 as comprising plate holder assembly 50, as well as swivel 80 and tong end 32 (or a part of the distal portion of upper tong 30). Releasable component 100 may be detached and attached to clamp 10 by release mechanism 110. Different types of release mechanisms 110 of the current invention are described below.

Figure 8:
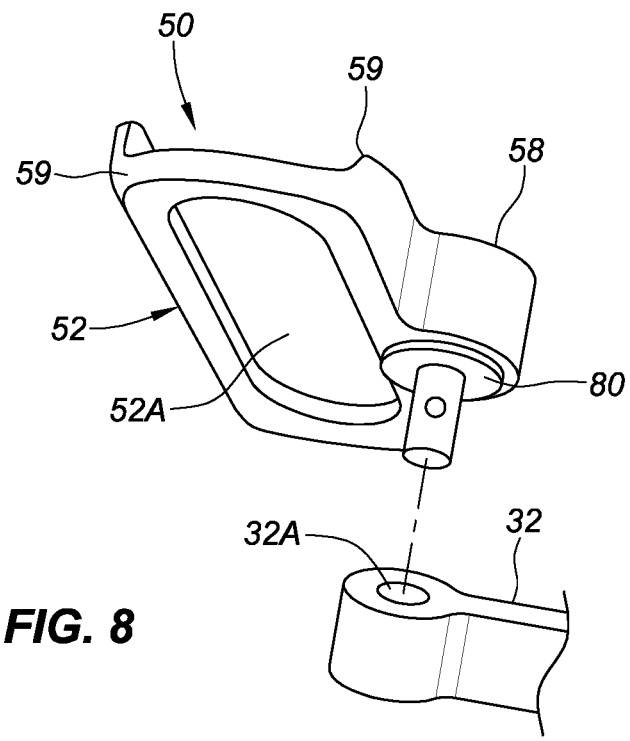
FIG. 8 shows an exploded view of a release mechanism involving a pin and ball that engages a bored hole.
Figure 8A:
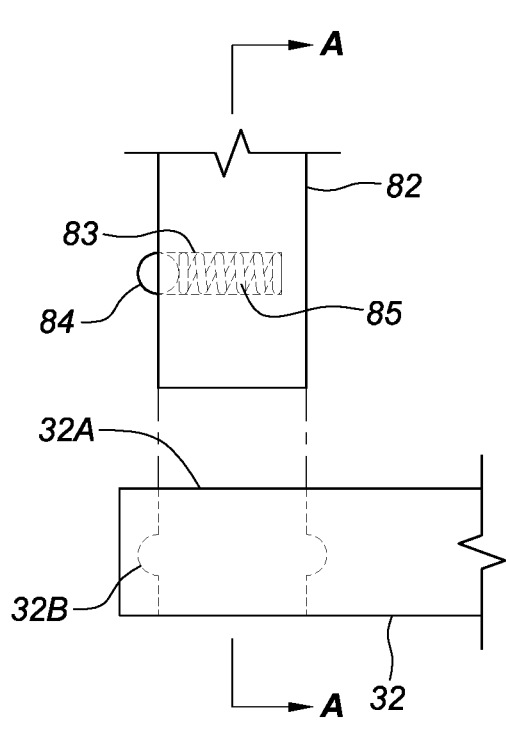
FIG. 8A is a side view of the release mechanism of FIG. 8.
Figure 8B:
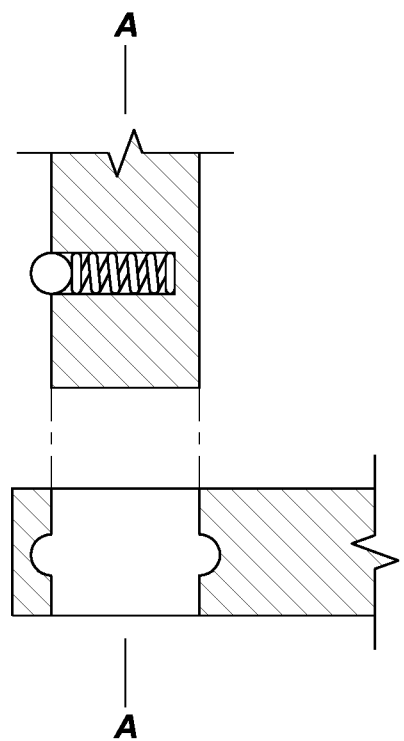
FIG. 8B is a section view of the release mechanism of FIG. 8.
Figure 11A:
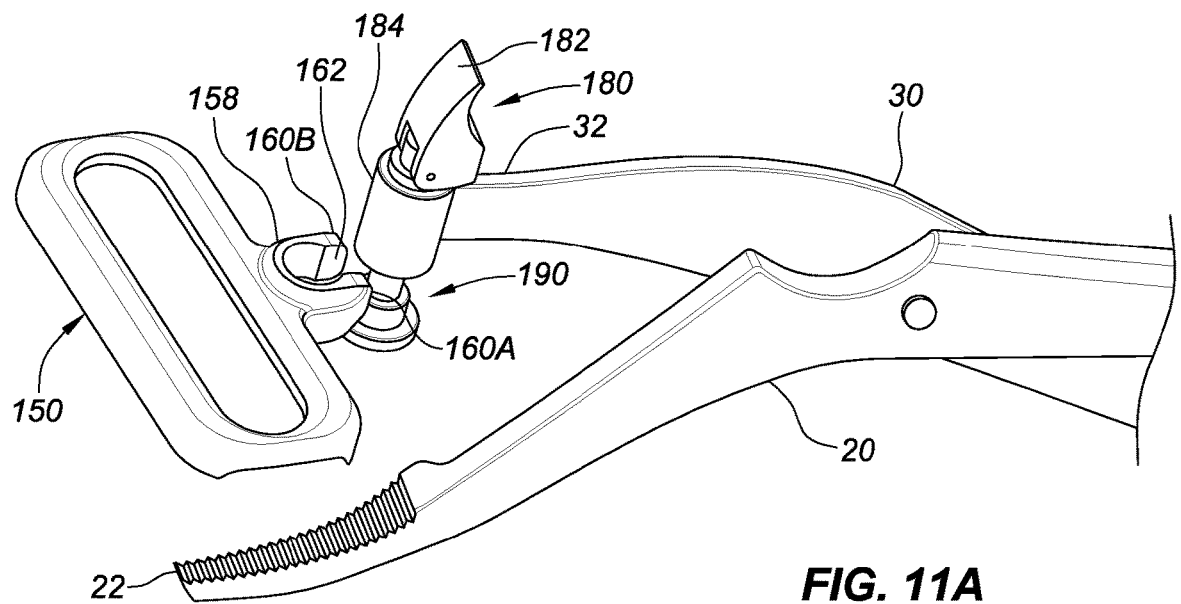
FIGS. 11A-11B are perspective views showing a releasable frame detached from a release mechanism with a pin in an extended position.
Figure 11B:
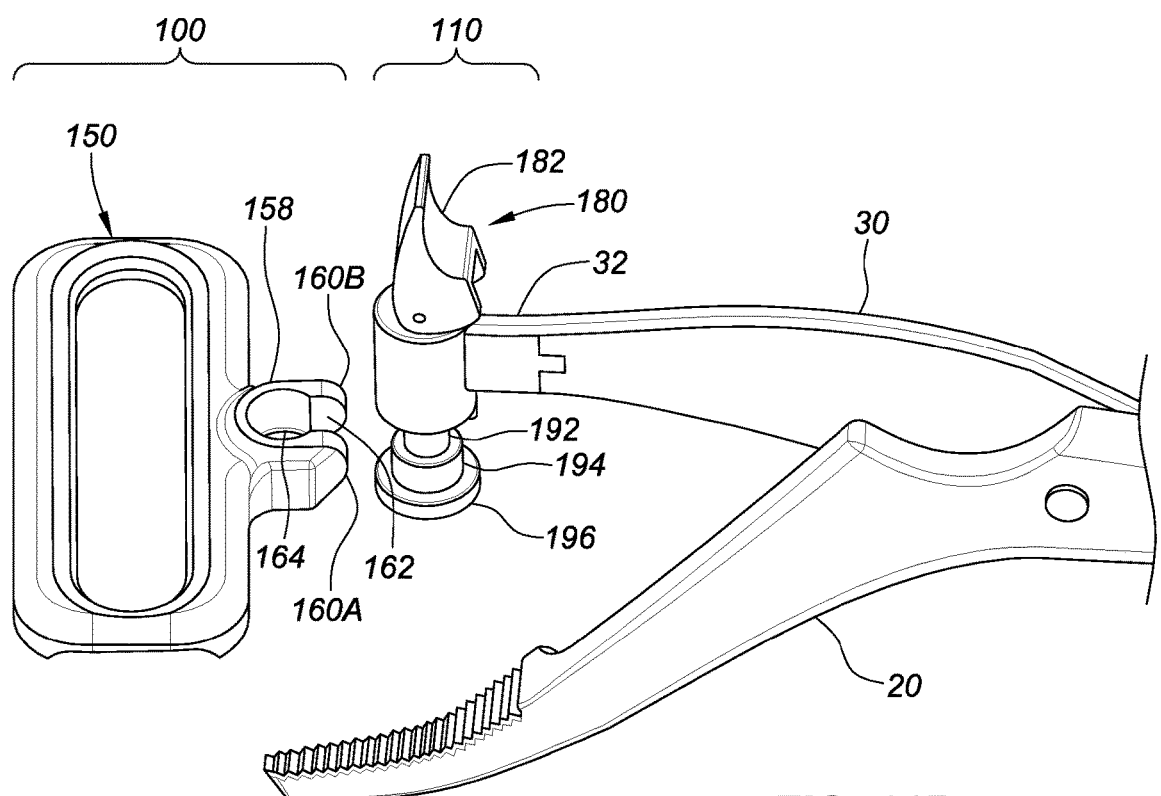
Figure 12:
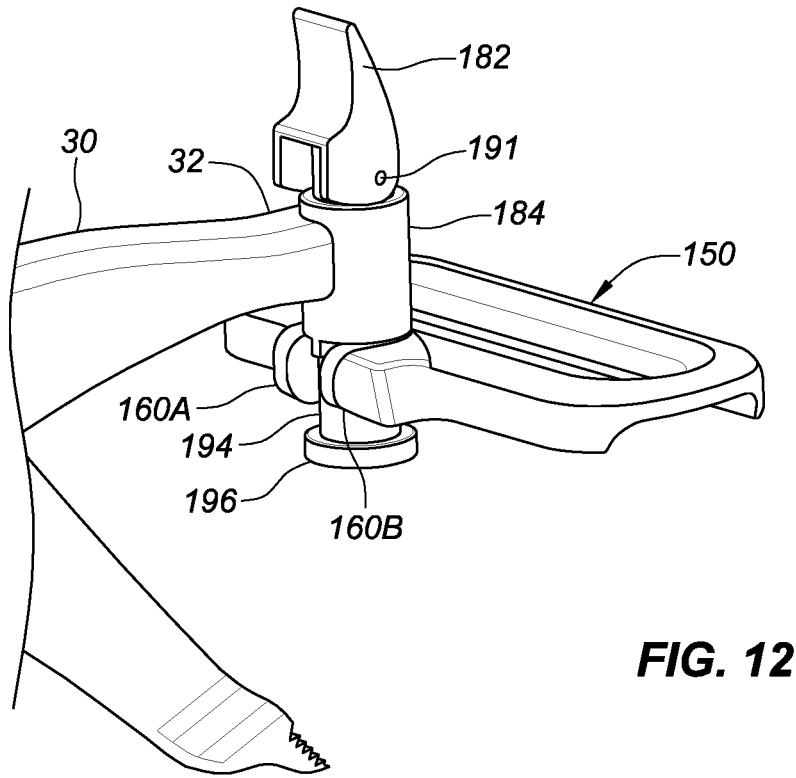
FIG. 12 is a perspective view showing a releasable frame engaging a release mechanism with a pin in an extended position.

Alternatively, releasable component 100 may comprise plate holder 50, tab 58 and swivel 80 as shown in FIGS. 8, 8A and 8B. In this embodiment, releasable component 100 does not include tong end 32; instead, releasable component 100 may be detached from tong end 32. It is preferred that plate holder assembly 50 may still swivel relative to tong end 32.

In this embodiment, release mechanism 110 may include pin 82 that extends from tab 58 and swivel 80 and that engages hole 32A located at or near distal end 32. Pin 82 may be inserted into hole 32A, but may also be released therefrom. As such, pin 82 may replace the bolt or screw or other attachment means mentioned above; and hole 32A may replace the threaded hole 38. The wall of hole 32A may also include a groove 32B.

Different types of release mechanisms 110 may exist between swivel 80 and distal end 32, but in an embodiment shown in FIGS. 8A-8B, pin 82 may include a hole or bore 83 that extends laterally and that accommodates a ball bearing 84 that may protrude from the surface of pin 82. Ball bearing 84 may be spring loaded, i.e., a spring 85 may be positioned between the ball bearing 84 and the end of bore 83 so that ball bearing 84 is biased outward and protrudes from the surface of pin 82.

When pin 82 is initially inserted into hole 32A, ball bearing 84 may be pushed inward so that pin 82 may be further inserted into hole 32A. However, when pin 82 has been sufficiently inserted, ball bearing 84 may engage groove 32B. The bias of spring 85 may push ball bearing 84 into groove 32B thereby securing releasable portion 100 to clamp 10.

Groove 32B may extend around the circumference of the wall of hole 32A so that ball bearing 84 may slide therein, thereby allowing frame holder assembly 50 to rotate relative to clamp 10. As such, pin 82 may be fixedly secured to swivel 80 because the rotation may be provided between ball 84 and groove 32B. Alternatively, a swivel arrangement 80 may exist between pin 82 and tab 58.

It is preferred that the force exerted by spring 85 is sufficient to ensure that the engagement between releasable portion 100 and clamp 10, i.e., the release mechanism 110, is sufficiently secure to withstand the forces exerted by the surgeon during surgery so that frame 52 securely positions plate 90 over the fractured boned ends. It is also preferred that releasable portion 100 may still be readily detached from tong end 32. That is, it is preferred that the bias of spring 85 is not so great so as to prevent ball bearing 84 from being retracted into bore 83 when the surgeon pulls up on releasable portion 100 to detach it from tong end 32.

In an alternative of the embodiment shown in FIGS. 8, 8A and 8B pin 82 extends from tong end 32 and a hole with a groove is formed in tab 58/swivel 80. This embodiment operates similarly as in FIGS. 8, 8A and 8B, where the components of release mechanism 110 are inverted.

Another embodiment of release mechanism 110 that comprises a magnetic lock 120 is now described with reference to FIGS. 9A and 9B. In this embodiment, releasable portion 100 may comprise plate holder assembly 50, tab 58, swivel 80 and a portion of distal end 32 of tong 30, as well as insertion end 126. Insertion end 126 preferably comprises a ferrous material that is attracted by a magnetic field. Magnetic lock 120 may include a receptacle 124 that receives the insertion end 126. Magnetic lock 120 may also include an electromagnet through which an electric current may pass. The current, which may be provided by a battery or other power source (not shown), creates a magnetic charge that attracts the ferrous insertion end 126, thereby locking it in place within receptacle 124 as shown in FIG. 9B.

Magnetic lock 120 may include a release button 122 that may be pressed to release insertion end 126 from receptacle 124. When release button 122 is pressed, it may interrupt the current, thereby removing the magnetic field that attracts insertion end 126, thereby allowing releasable portion 100 to detach from clamp 10.

Another embodiment of release mechanism 110 that comprises a collet 130 is now described with reference to FIGS. 10A and 10B. In this embodiment, releasable portion 100 may comprise plate holder assembly 50, tab 58, swivel 80 and a portion of distal end 32 of tong 30, as well as insertion end 136. Collet 130 may include tapered receiving sleeve 132, e.g., Morse Taper, that may include springs 133A and slots 133B around its circumference, where the ends of springs 133A form receptacle 134. Springs 133A may extend radially outward along their length to their ends. Collet 130 also includes ring or other clamping device 135 that may slide along the length of sleeve 132.

After insertion end 136 is inserted into receptacle 134, ring 135 may be moved distally thereby clamping down on springs 133A, thereby decreasing the diameter of receptacle 134, which in turn clamps down on insertion end 136. This preferably secures insertion end 136 within sleeve 132, and thus secures releasable portion 100 within collet 130 as shown in FIG. 10B.

Ring or other clamping device 135 may be spring-biased distally. As such, the surgeon may retract ring 135 proximally, insert releasable portion 100, i.e., insertion end 136, into receptacle 134, and then release ring 135 which secures releasable portion 100 to clamp 10 as it moves distally along sleeve 132. To detach releasable portion 100 from clamp 10, the surgeon may retract ring 135, thereby allowing springs 133A to expand and to release their grip on insertion end 136.

In a preferred embodiment, the shape of the pin of frame assembly 50 that is inserted into the receptacle of the release mechanism, as well as the shape of the receptacle that receives the pin may be something other than circular. This way the pin preferably does not rotate within the receptacle after the release mechanism is locked.

Another embodiment of release mechanism 110 that comprises a lever or flip switch assembly 180 is now described with reference to FIGS. 11A-B, 12, 13, 14A-C, 15A-B and 16. In this embodiment, releasable portion 100 may comprise plate holder assembly 150 that may include tab 158. Lever or flip switch assembly 180 may include lever 182 and extendable retractable pin 190. As discussed below, pin 190 may be extended to receive tab 158 of frame assembly 150. Once tab 158 and pin 190 have engaged, lever 182 may be flipped thereby retracting pin 190 and locking frame assembly 150 in place.

Figure 14A:
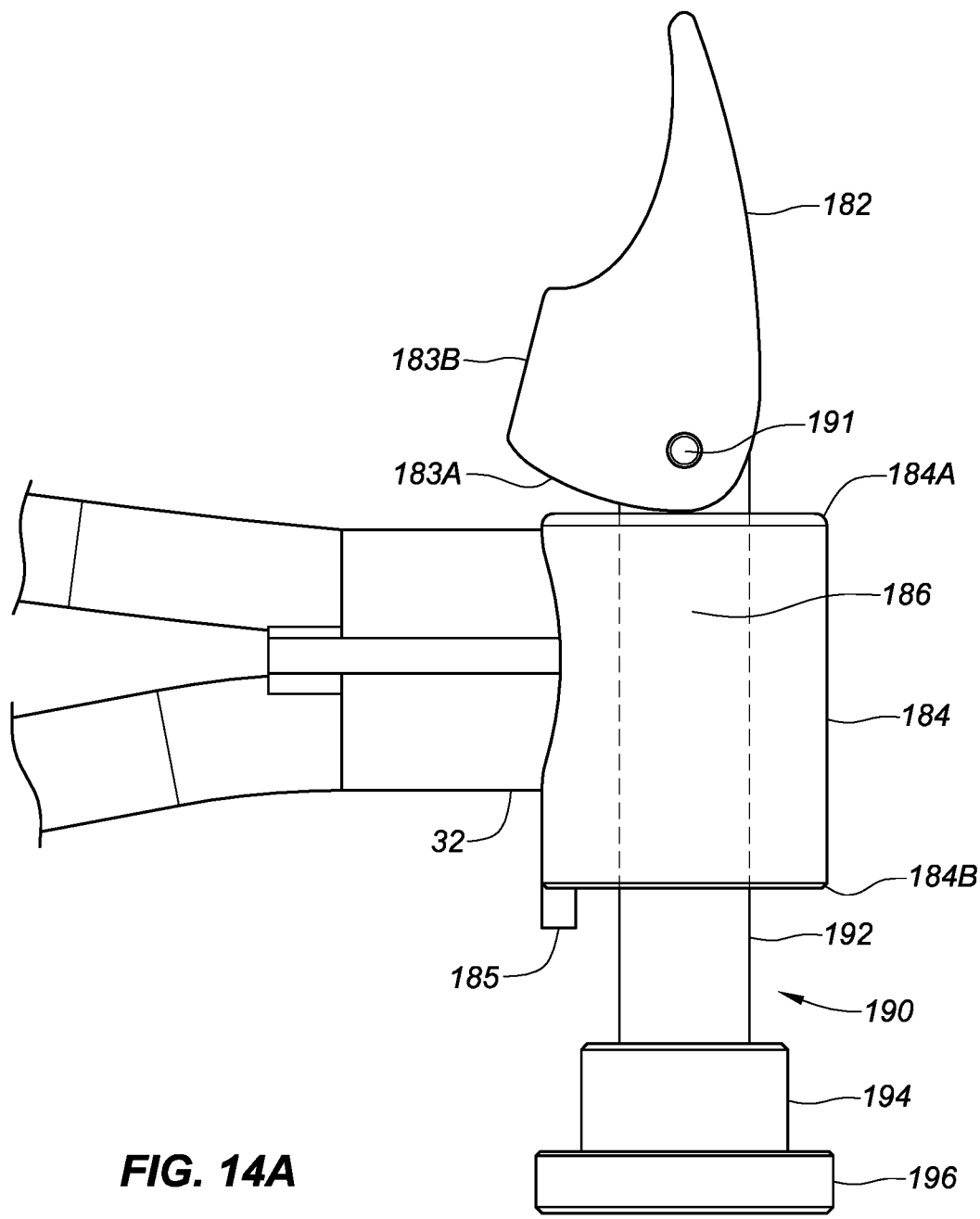
FIGS. 14A-C are side views of a release mechanism with a pin in an extended position, partially retracted/extended position and retracted position, respectively.
Figure 14B:
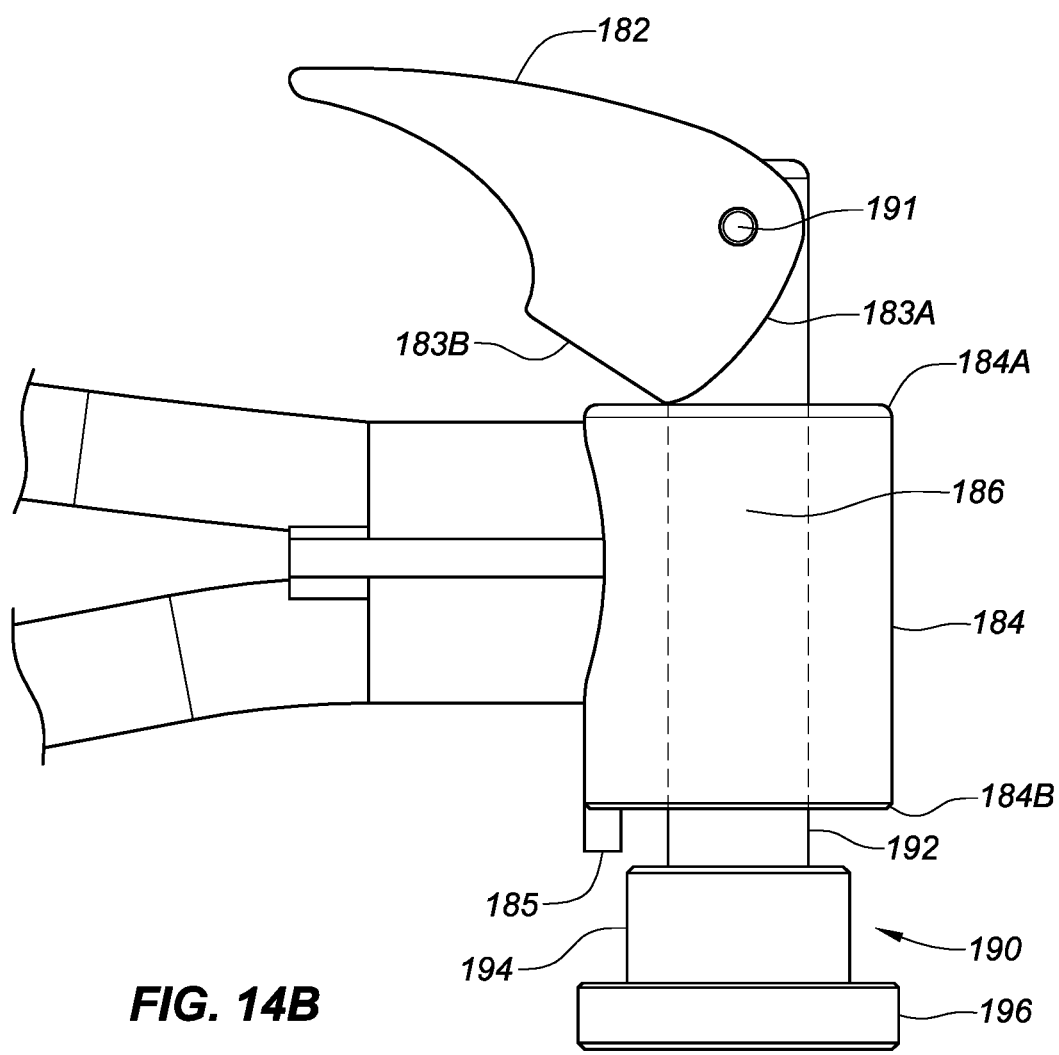
Figure 14C:
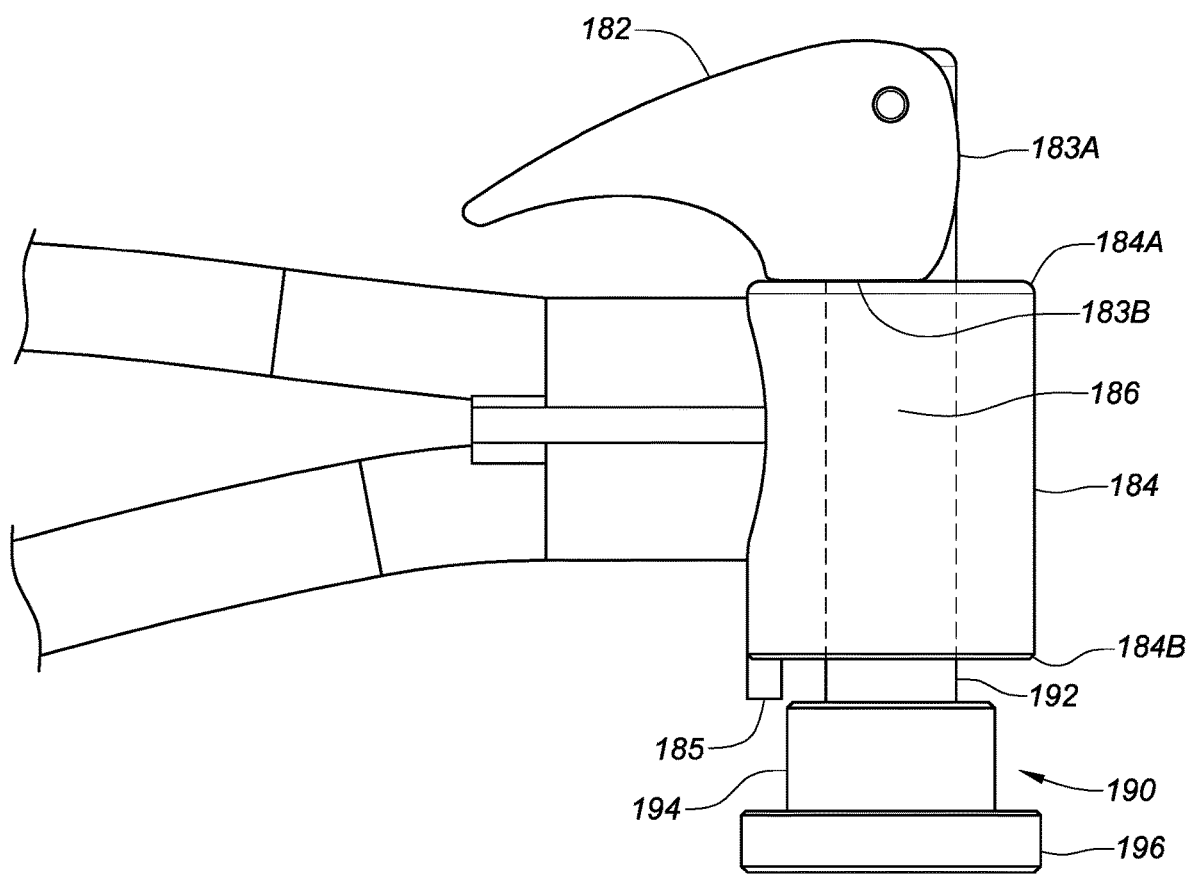
Figure 15A:
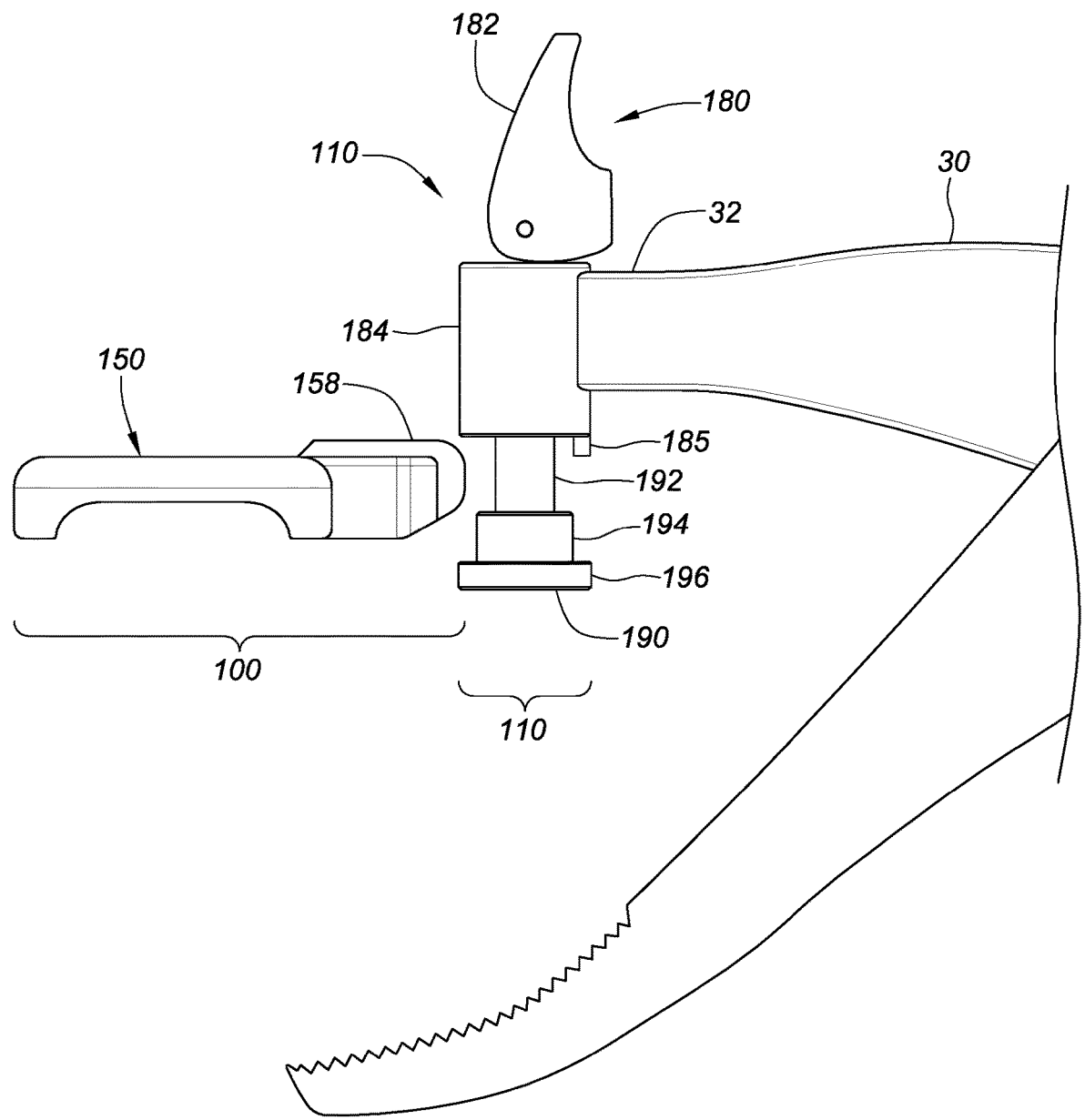
FIGS. 15A-B are side views showing a release mechanism in an open position along with a detached frame, and the frame engaged with the release mechanism in a closed position.
Figure 15B:
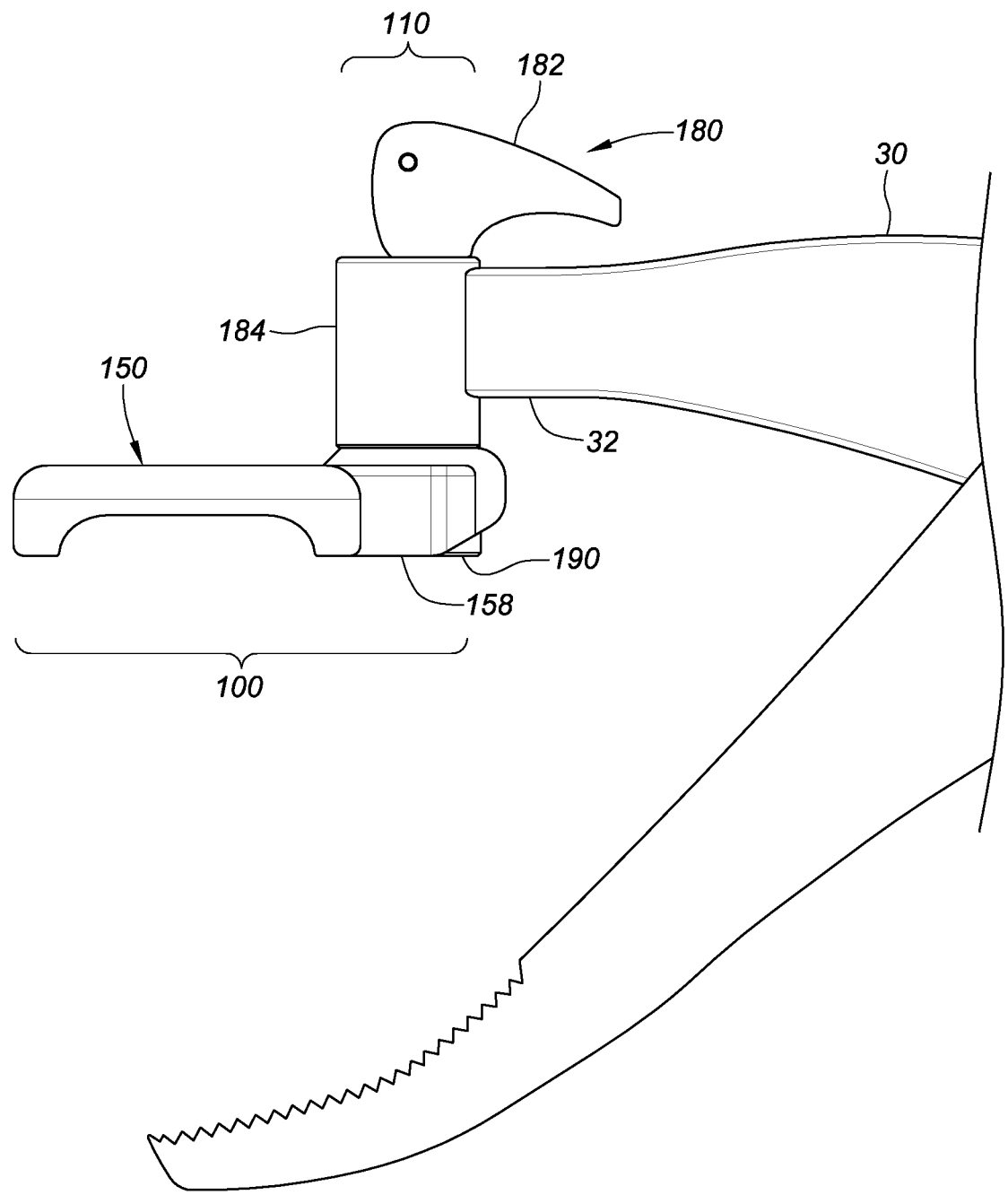

Flip switch assembly 180 is now described in more detail. Assembly 180 may include housing 184 which may be located at distal end 32 of upper tong 30; housing 184 may be integrally formed as part of upper tong 30 or may otherwise be attached thereto. As shown in FIGS. 14A-C, housing 184 preferably includes bore 186 through which extendable/retractable pin 190 movably extends or retracts.

Lever 182 may reside on top of housing 184 and may be rotatably coupled to pin 190 via pin 191, so that it may move from an open position as in FIG. 14A, to an intermediate position as in FIG. 14B to a closed position as in FIG. 14C. Lever 182 may include a curved or cam surface 183A that controls the extension or retraction of pin 190 as lever 182 rotates about pin 191. Lever 182 may also include flat surface 183B that generally maintains lever 182 in closed position with pin 190 retracted. Housing 184 may also include tab 185 which is described in more detail later.

Pin 190 may include several sections having different diameters, such as upper section 192 which may have a relative small diameter, a middle section 194 which may have a larger diameter and a bottom or support section 196 which may have an even larger diameter. The functions of sections 192, 194, 196 are described in more detail in connection with tab 158 of frame assembly 150. Tab 158 may include prongs 160A, 160B separated by opening or slot 162. The width of slot 162 may generally correspond to the diameter of upper section 192 of pin 190. As such, when pin 190 is extended, and upper section 192 is exposed, frame assembly 150 may engage pin 190 by passing upper section 192 through slot 162.

Tab 158 may also include bore or hole 164 which may have a diameter generally corresponding to the diameter of middle section 194 of pin 190. As such, when lever 182 is moved towards its closed position, and pin 190 retracts into housing 184 and moves upward in relation to tab 158, middle section 194 generally engages hole 164. At the same time, because the width of slot 162 is smaller than the diameter of middle section 194, tab 158 and frame assembly 150 are now generally attached to release mechanism 110. And because the diameters of hole 164 and middle section 194 generally correspond, or are the same or near the same, frame assembly 150 may be securely (but releasably) attached to pin 190 and release mechanism 180.

Figure 13:
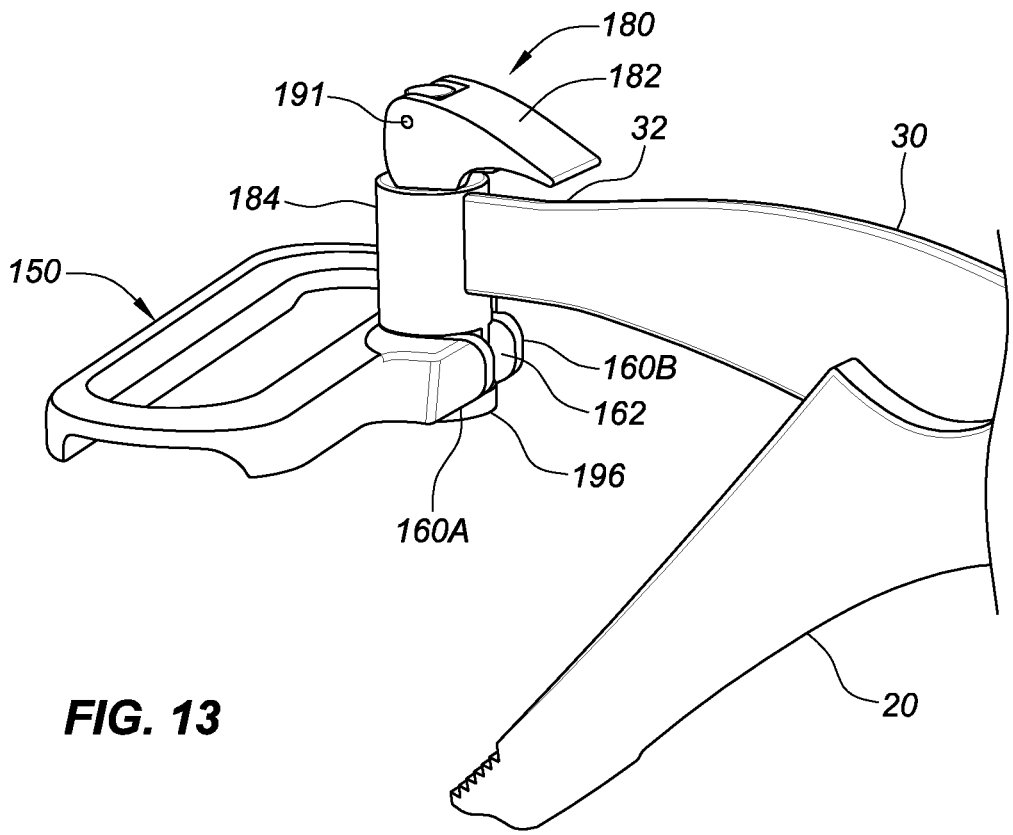
FIG. 13 is a perspective view showing a releasable frame attached to a release mechanism with a pin in a retracted position.
Figure 16:
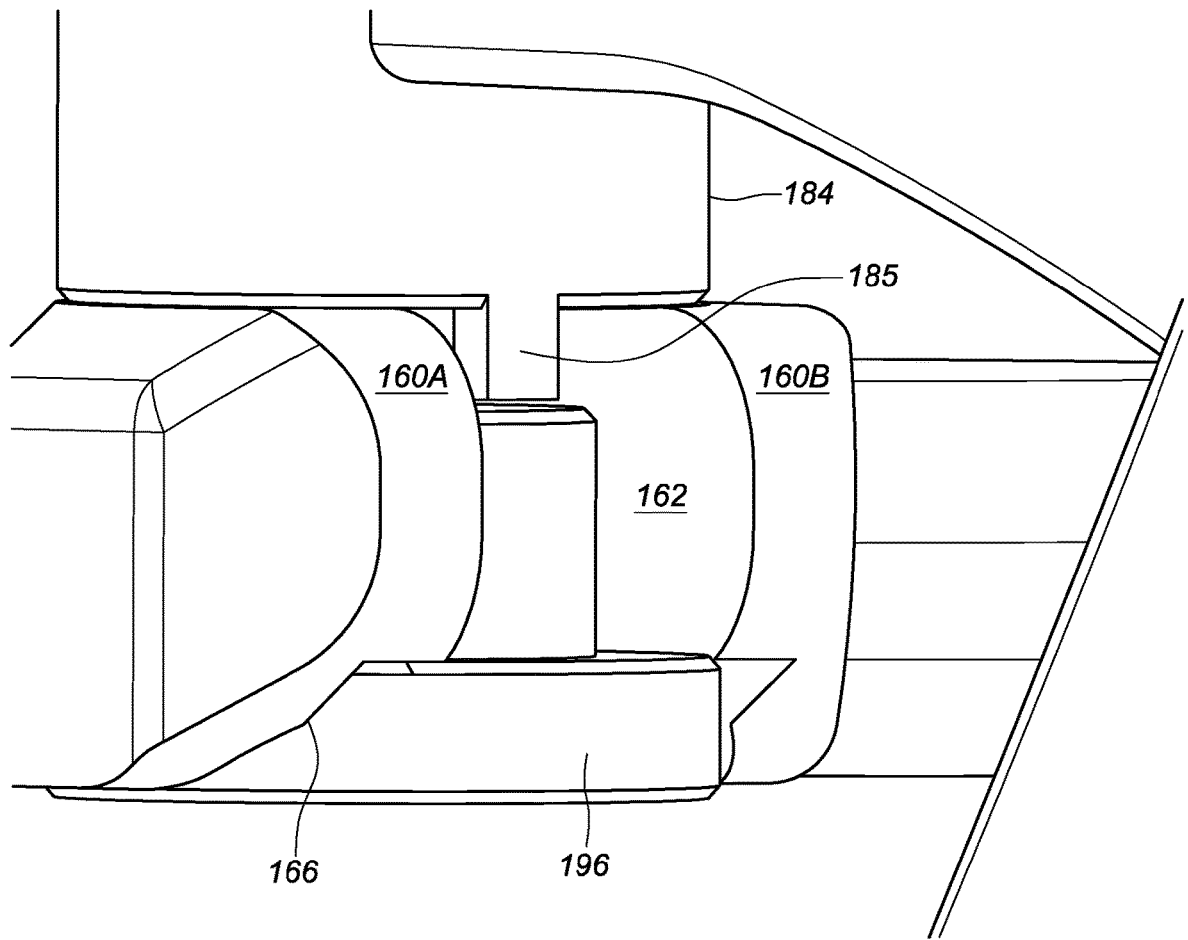
FIG. 16 is a side view showing a frame engaging a release mechanism in a closed position.

Tab 158 may also include seat or bottom annular cutout 166 which may have a diameter generally corresponding to the diameter of lower section 196 of pin 190. As such, when lever 182 is moved towards its closed position and pin 190 retracts into housing 184 and upward relative to tab 158, lower section 196 generally engages bottom seat 166 as best shown in FIGS. 13 and 16. When so engaged, lower section 196 preferably supports frame assembly 150 from the bottom. Furthermore, because the diameters of seat 166 and lower section 196 generally correspond, or are the same or nearly the same, their engagement also helps securely (but releasably) attach frame assembly 150 to release mechanism 180.

As noted above, housing 186 may include tab 185. When lever 182 is in the closed position, and frame assembly 150 or releasable portion 100 is engaged with pin 190, tab 185 may be positioned in slot 162 between prongs 160A, 160B. In one embodiment, the width of tab 185 may generally correspond to the width of slot 162, thereby providing another aspect of securing tab 158 to pin 190 and thus securing releasable portion 100 to release mechanism 110.

An advantage of this embodiment is that releasable portion 100 is secured to release mechanism 110 in several different ways, thereby providing a secure engagement that may withstand the forces imparted on clamp 10 during a surgery. That is, the engagement between the surfaces of hole 164 and middle section 194 preferably prevent or reduce any play between frame assembly 150 and pin 190. Furthermore, the engagement between the surfaces of seat 166 and lower section 196 also preferably prevent or reduce any play between frame assembly 150 and pin 190; and lower section 196 provides support from the bottom. Still further, prongs 160A, 160б may engage tab 185 to further avoid or reduce any play.

The foregoing multiple aspects of securing frame assembly 150 to clamp 10 preferably allows the surgeon to expert whatever clamping force is necessary to clamp 10 during surgery, without frame assembly 150 wiggling with respect to tong distal end 32 or clamp 10. This in turn preferably allows the surgeon to position the plate or other fixation device 90 with a higher degree of precision and confidence.

As with other embodiments described above, it is also preferred that frame assembly 150 may swivel or rotate in relation to release mechanism 110, to allow the surgeon to rotate clamp 10 out of the way when, e.g., inserting the screws into plate 90 to fix plate 90 to the patient's bone. In the embodiment of FIGS. 11-16, this swiveling or rotation may occur in different ways.

For example, housing 186 may include a bearing or swivel that allows pin 190 to rotate therein, thereby allowing clamp 10 to rotate or swivel out of the way relative to frame assembly 150 when frame assembly 150 is in the desired position to hold plate 90 in place. In this embodiment, housing 184 may include top 184A and bottom 184B that rotate relative to housing 184, where lever 182 may rotate along with top 184A, and where tab 185 may rotate along with bottom 184B. In this embodiment, the multiple aspects of securing frame assembly 150 to pin 190 exist while frame assembly 150 rotates along with pin 190.

As another example, pin 190 does not rotate within housing 184 but frame assembly 150 may rotate relative to pin 190. Here, while the engagement between the surfaces of hole 164 and middle section 194 may still engage each other, they may still allow some amount of movement between them. The same may apply for the engagement between the surfaces of seat 166 and lower section 196. And in this example, the width of tab 185 may be less than the width of slot 162, thereby allowing rotation before either of prongs 160A, 160б engages tab 185.

Alternatively, the releasable frame assembly 150 of FIGS. 11-16 need not rotate or swivel, but may still be releasable. Here, when lever 182 is in a closed position and pin 190 is retracted upward, frame assembly 150 may be locked in place.

As noted above, the current invention is not limited to the release mechanisms 110 shown in FIGS. 8-16. Instead, the current invention includes any mechanism that may readily release the component(s) comprising releasable portion 100 so as to facilitate efficient surgeries, and preferably reduce surgery time and time during which the patient is under anesthesia. It is also preferred that the quick release mechanism be compact or otherwise not interfere with the use of clamp 10. In a preferred embodiment, a keyless drill chuck with a secondary lock mechanism may be used.

The current invention may provide these benefits especially where the actual circumstances and requirements of the surgery are revealed only after incisions are made and the fracture site is opened, and these actual circumstances and requirements turn out to be different than what the pre-surgery x-ray indicated. In this situation, the modularity of the current invention allows the surgeon to quickly adapt by readily changing the plate and plate holder that are necessary for the surgery.

The modular nature of clamp 10 provides advantages beyond efficiency and reduced time for surgery. For example, releasable portion 100 may be suitable for only one or a limited number of surgeries because the forces exerted on it by the surgeon when reducing a fracture and maintaining the reduction while the plate is installed may damage or otherwise wear out the frame 52 or frame holder assembly 50. Furthermore, it may be more economical to dispose of the releasable portion 100 rather than sterilize it for additional use in additional surgeries. However, the rest of clamp 10 may be readily reusable for multiple surgeries because, e.g., it is less prone to damage or wearing out. Because the tongs 20, 30 and the rest of clamp 10 have a cost associated with them, the fact that they may be reused while the releasable portion is disposed of represents a cost savings. That is, rather than discard the entire clamp 10, only the releasable portion 100 may be discarded.

The modularity of the current invention may also provide cost savings as follows. While the releasable portion 100 may be suited for only certain types of surgeries, e.g., reducing fractures and installing plate 90 on certain size bones, the tongs 20, 30 and the rest of clamp 10 may be suited to use for different types of surgeries. That is, a given set of tongs 20, 30 may be used with different types of frames 50 to install different types of plates 90. The modularity of the current invention avoids the need for purchasing a complete clamp 10 for each type of surgery. Instead, only the releasable portions 100 may need to be purchased.

For example, the current invention is suitable for installing plates 90 for various types of fractures, e.g., fibula, tibia, tibia plateau, femur, supra condylar femur, forearm, humerus and clavicle. A number of differently sized plates 90, and thus a number of differently sized or configured frames 50 (and releasable portions 100) may be needed to perform these surgeries. However, a given set of tongs 20, 30 may be reused for some number of these different types of surgeries. And even where a given set of different types of surgeries may require more than one set of tongs 20, 30, the current invention still allows a surgery center, hospital or other facility to avoid purchasing a set of tongs 20, 30 for each different type of surgery.

The materials from which components comprising releasable portion 100 and clamp 10, as well as plate 90, are made are now further described. In certain surgeries, it may be desirable to take an x-ray while the surgery is being performed and while releasable portion 100 and/or other parts of clamp 10 may be within the patient. Also, x-rays are typically taken after surgery to gauge healing. However, plates and other fixation devices, as well as the clamps used to install them, have typically been made of metals which are opaque to x-rays and thus obstruct the x-ray visibility of, e.g., the position of fractured bone ends that may be located behind a plate or the clamp used to install the plate.

To address the foregoing drawbacks, frame holder assembly 50 and/or other components comprising releasable portion 100 or clamp 10 may comprise radiolucent materials such as polyether ether ketone (PEEK) or carbon-fiber reinforced materials. These materials do not interfere with medical imaging provided by MRI, CT and x-ray scans. As such, the materials comprising the current invention preferably allow an x-ray taken during surgery to provide, for example, a clear image of the positioning of the fractured bone ends during open reduction surgery. It is also preferred that the translucent materials comprising frame holder assembly 50, releasable portion 100 and/or clamp 10 reflect sufficient strength while avoiding excess brittleness. For example, carbon fibers are very brittle, but the current invention includes the use of carbon-fiber reinforced thermoplastics. This composite material provides sufficient strength as well as an amount of flexibility.

The materials that may comprise clamp 10 are now more fully described. In an embodiment of the current invention, clamp 10 may comprise surgical stainless steel, including tongs 20, 30 and frame assembly 50. Alternatively, such as in embodiments including a releasable portion 100, tongs 20, 30 may still comprise surgical stainless steel and frame assembly 50 and/or releasable portion 100 may comprise polyphenylsulfone (PPSU), polyetherimide (PEI), polyetheretherketone (PEEK) or carbon fiber reinforced polyketone or polyether etherketone.

Such materials may be used because they provide a combination of strength to withstand the clamping forces exerted by the surgeon, flexibility to avoid excessive brittleness, biocompatibility, and as noted above, radiolucency.

Although certain presently preferred embodiments of the invention have been described herein, it will be apparent to those skilled in the art to which the invention pertains that variations and modifications of the described embodiments may be made without departing from the spirit and scope of the invention.

What is claimed is:

1. A device to assist in surgery, comprising:
 a first tong that includes a distal end which is configured to engage a fractured bone;
 a second tong that includes a distal end, and that is moveably coupled to the first tong;
 a holder that is moveably coupled to the distal end of the second tong, that is configured to position a fixation plate between the holder and the fractured bone, and that includes a frame surrounding an opening which provides access to the fixation plate;
 wherein the frame is sized to engage edges of the fixation plate;
 wherein the frame includes two sides and two ends;
 wherein the two sides form lips that engage two edges of the fixation plate; and
 wherein the two ends form lips that engage two other edges of the fixation plate.

2. The device of claim 1, wherein the holder is moveably coupled to the distal end of the second tong by a swivel.

3. An orthopedic clamp for assisting with open fracture reduction surgery, comprising:
 a first tong that includes a distal end which is configured to engage a fractured bone;
 a second tong that is movably coupled to the first tong and that includes a release mechanism;
 a releasable portion that is releasably attached to the release mechanism, wherein the releasable portion includes a frame that is configured to position a fixation plate between the frame and the fractured bone; and
 wherein the release mechanism includes a lever or flip switch assembly with an extendable and retractable pin that engages the frame.

4. The orthopedic clamp of claim 3, wherein the frame is rotatable relative to the second tong.

5. The orthopedic clamp of claim 3, wherein the frame comprises polyphenylsulfone, polyetherimide, polyether etherketone or a carbon fiber reinforced polyketone or polyether etherketone.

6. The orthopedic clamp of claim 3, further comprising a swivel, positioned between the frame and the second tong, wherein the swivel allows the frame to rotate relative to the second tong.

7. The orthopedic clamp of claim 3, wherein the frame includes a tab having a slot and a hole and the pin has a first diameter that corresponds to the slot and a second diameter that corresponds to the hole.

8. The orthopedic clamp of claim 7, wherein the release mechanism includes a tab having a width that corresponds to the width of the slot.

9. The orthopedic clamp of claim 7, wherein the tab includes a bottom seat and the pin includes a third diameter that corresponds to the bottom seat.

10. The orthopedic clamp of claim 3, wherein the lever or flip switch assembly includes a housing attached to the second tong, and the pin is rotatable within the housing.

11. An orthopedic clamp for assisting with open fracture reduction surgery, comprising:
 a first tong that includes a proximal end having a handle and a distal end which is configured to engage a fractured bone or bone ends;
 a second tong that includes a proximal end having a second handle, a mechanism rotatably attaching the second tong to the first tong, and a release mechanism, wherein the release mechanism includes a keyless chuck having a non-circular receptacle; and
 a releasable portion that includes:
  a holder which comprises a radiolucent material and which is configured to position a fixation plate between the holder and the fractured bone or bone ends;
  a swivel that is connected to the holder and that allows the holder to rotate relative to the second tong; and
  a pin that is connected to the swivel and that has a non-circular cross-section which releasably engages the receptacle.

12. The orthopedic clamp of claim 11, wherein the release mechanism includes a secondary lock mechanism.

13. The orthopedic clamp of claim 12, wherein the holder includes a frame comprising a polyphenylsulfate, polyetherimide, polyether etherketone or a carbon fiber reinforced polyketone or polyether etherketone material.

14. The orthopedic clamp of claim 13, wherein the frame surrounds an opening which provides access to the fixation plate.

15. The orthopedic clamp of claim 13, wherein the frame includes one or more lips that engage one or more edges of the fixation plate.

\* \* \* \* \*